US006905706B2

(12) United States Patent
Wikman et al.

(10) Patent No.: US 6,905,706 B2
(45) Date of Patent: *Jun. 14, 2005

(54) MEDICINAL HERBAL EXTRACT CARPEDIOL FOR TREATING DEPRESSION

(75) Inventors: Georg Wikman, Askloster (SE); Alexander Panossian, Yerevan (AM)

(73) Assignee: Swedish Herbal Institute, Göteborg (SE)

( * ) Notice: Subject to any disclaimer, the term of this patent is extended or adjusted under 35 U.S.C. 154(b) by 289 days.

This patent is subject to a terminal disclaimer.

(21) Appl. No.: 10/124,132

(22) Filed: Apr. 16, 2002

(65) Prior Publication Data

US 2003/0194449 A1 Oct. 16, 2003

(51) Int. Cl.[7] .............................. A61K 9/20; A61K 9/14; A61K 35/78
(52) U.S. Cl. .................. 424/464; 424/489; 424/725
(58) Field of Search ................................ 424/464, 489, 424/725

(56) References Cited

U.S. PATENT DOCUMENTS 6,399,116 B1 * 6/2002 Xiu ............................ 424/773

FOREIGN PATENT DOCUMENTS

SU        1725109 A1 *  4/1992  .......... G01N/30/06

OTHER PUBLICATIONS

Subhuti Dharmananda, Tibetan Herbal Medicine, May 2001.*
Abidoff Musa, et al., Effect of *Rhodiola Rosea* and *Rhodiola Crenulata* (*Crassulaceae*) Root Extracts on ATP Content in Muscle Mitochondria, 2002, Ameriden International.*

Judd, Mood disorders in the general population represent an important and worldwide public health problem, International Clinical Psychopharmacology, 1995; 10 Supp. 4: 5–10.
Korff et al., Anxiety and Depression in a Primary Care Clinic, Arch Gen Psychiatry, 1987; 44:152–156.
Wells et al., Psychiatric Disorder in a Sample of the General Population with and without Chronic Medical Conditions, Am J Psychiatry, Aug. 1988; 145(8): 976–981.
Lumpkin and Alpert, FDA Public Health Advisory, Feb. 10, 2000.
Steinegger–Hausel, Farmalignosie, 1992; 613.
Ssaratikov et al., Rhodiolosid, ein neues Glykosid aus Rhodiola rosea und seine pharmakologischen Eigenschaften, Die Pharmazie, 1968; 7:392–395.
Sammanfattningar av bibliografiska data, no date.
Hoeg, Rosenrot og Smorbukk, Vare Medisinske Planter, 1984; 466.
Roselli, En Liten Dock Mycket Nyttig Ortabok eller Den Lille Naturlakaren, De Gamla Folkbockerna, 1974; 9:62–65, no date.
Olsson et al., Rosenrot, Ortmedicin och vaxtmagi, 1988; 233.
Sandberg and Bohlin, Vaxtbaserade Iakemedel, Fytoterapi, 1960.

(Continued)

*Primary Examiner*—James M. Spear
(74) *Attorney, Agent, or Firm*—JHK Law; Joseph Hyosuk Kim

(57) ABSTRACT

The present invention is directed to anti-depressive activity of Crassulaceae special extracts, Carpediol, containing 2-(4-hydroxyphenyl)ethyl-β-d-glucopyranoside or 3-[6-o-(α-1-arabinopyranosyl)-β-d-glucopyranosyl]-oxy-1-phenylpropene in mammals, to method of preparation and analysis of these extract, as well to safety of their usage in combination with other drugs.

19 Claims, 6 Drawing Sheets

OTHER PUBLICATIONS

Pharmacopee Francaise, 1974; 2:100–101.

Linnaei, Materia Medica., 1749; 14:168–169.

Virey, Theorique Et Pratique, Traite de Pharmacie., 11:38–39, 68–71, 80–81, 90–93.

Saratikov, Some Results in the Search and Study of Herbal Stimulants of the Central Nervous System, CNS Stimulants., 1966; 1–14.

Tsarong, Handbook of Traditional Tibetan Drugs Their Nomenclature, Composition, Use and Dosage, Tibetan Medical Publications, 1986; 1:1–101.

Muravijeva, Pharmacognosy (with fundamentals of biochemistry of medicinal herbs), Meditsina, 1978; 1–9.

Mashkovskij, Medicines, Meditsina, 1977; 1,2:1–6, 131–134.

Turova and Sapozhnikova, Medicinal Plants of the USSR and Their Use, Meditsina, 1984; 4:3–4, 29–37.

Muller–Dietz et al., Arzneipflanzen in der Sowjetunion, Medizinische Folge Herausgegeben., 1969; 44:91–93.

Wagner et al., Plant Adaptogens, Phytomedicine., 1994; 1:63–76.

Brekhman and Dardymov, New Substances of Plant Origin which increase nonspecific resistance, Annual Reviews, 1969; 9:419–430.

Azizov and Seifulla, The Effect of Elton, Leveton, Phytoton, and Adapton on the Working Capacity of Experimental Animals, Tom., 61: 61–63, no date.

Porsolt et al., Behavioural Despair in Rats: A new model sensitive to Antidepressant Treatments, European Journal of Pharmacology, 1978; 47:379–391.

Porsolt et al., Behavioural Despair in Mice: A Primary Screening Test for Antidepressants, Arch. int. Pharmacodyn, 1977; 229: 327–336.

Porsolt et al., Depression: a new animal model sensitive to antidepressant treatments, Nature, 1977; 266: 730–732.

Chatterjee et al., Antidepressant Activity of *Hypericum Perforatum* and Hyperforin: the Neglected Possibility, Pharmacopsychiat; 1998; Supp. 31:7–15.

Bhattacharya et al., Activity Profiles of Two Hyperforin–Containing hypericum Extracts in Behavioral Models, Pharmacopsychiat, 1998; 31:22–29.

Butterweck et al., Flavonoids from *Hypericum perforatum* Show Antidepressant Activity in the Forced Swimming Test, Planta Medica, 2000; 66:3–6.

Theophylline, Supplied by the British Library– www.bl.uk ., 78–81, no date.

Biber et al., Oral Bioavailability of Hyperforin from Hypericum Extracts in Rats and Human Volunteers, Pharmocopsychiat, 1998, 31:36–43.

Ramzan and Levy, Kinetic of Drug Action in Disease States. XVI, Journal of Pharmacology and Experimental Therapeutics, 1986; 236(3):708–713.

Fugh–Berman, Herb–drug interactions, The Lancet, 2000; 355: 134–138.

\* cited by examiner

MEDICINAL HERBAL EXTRACT CARPEDIOL FOR TREATING DEPRESSION

BACKGROUND OF THE INVENTION

1. Field of the Invention

This invention relates to the field of antidepressive drugs. The invention is also related to a method of treating mild to moderate forms of depression by using a medicinal herbal extract of the Crassulaceae plant family.

2. Description of the Prior Art

It is well known that depressive disorders are disabling and common. More than 11% of the adult population is afflicted with depressive disorders. Most patients with depressive symptoms experience only mild or moderate depression, with different modalities like sleep disturbances, low self esteem, or somatic complaints. In such cases, it is more preferable to use antidepressive medication that is free of disturbing side effects associated with standard antidepressants like tricyclic or serotonin reuptake inhibitors (1–3).

By way of background, extracts of *Hypericum perforatum*, more commonly known as St. John's wort, have been popular during the last few years in Europe, particularly in Germany, as a drug of choice in treating mild depression. Recently, several reports concerning interactions of Hypericum with other drugs such as warfarin, theophylline, cyclosporine, anti-HIV drugs and oral contraceptives indicate that Hypericum induces a broad range of drug metabolizing enzymes, and thus Hypericum extracts should not be used concomitantly with certain medication (4).

Carpediol are special extracts made from plants belonging to the Crassulaceae family, especially those which can be found naturally in Sweden, Norway, Iceland, Finland and Northern Europe. The main active substance in these extracts are indicated to be 2-(4-hydroxyphenyl)ethyl-β-D-glucopyranoside and 3-[6-O-(α-L-arabinopyranosyl)-β-D-glucopyra-nosyl]-oxy-1phenylpropene (5, 6). Members of the Crassulaceae family have a tradition as medicinal plants in European and other countries (3–24). However, none of the prior art references discloses or suggests that extracts made from these plants and its components could have any anti-depressive activity. Moreover, none of the prior art references discloses or suggests that Carpediol extracts have minimal to no adverse effect on the pharmacokinetics of other drugs when used concomitantly with Crassulaceae.

Accordingly, there is a continuing need in the art for an anti-depressive medicine that works well with other drugs and does not show negative side effects.

SUMMARY OF THE INVENTION

The present invention has met the herein before described need.

The present invention is directed to a method for treating a symptom of depression comprising administering to a person in need thereof a composition comprising an extract of a plant belonging to Crassulaceae. The extract may comprise 2-(4-Hydroxyphenyl)ethyl-β-D-glucopyranoside or 3-[6-O-(α-L-arabinopyranosyl)-β-D-glucopyranosyl]-oxy-1-phenylpropene. These compounds may be present in an amount from about 2 to about 15 dry weight percent, about 5 to about 15 dry weight percent, or about 7 to about 15 dry weight percent.

The composition may be administered with another medicine, and the extract substantially has no effect on the pharmacokinetics of said additional medicine. The additional medicine may include without limitation, aminophylline or theophylline.

The method of the invention treats symptoms of depression such as insomnia, low self-esteem, emotional instability, or somatization, especially insomnia, emotional instability or somatization. According to the method of the invention, the symptom to be treated arises from mild to moderate form of depression.

In the method of the invention, the plant extracts may be from the genus *Sedum* or *Sempervivum*. The plant species include, but not limited to, *Sedum rosea, Sedum maximum, Sedum auglicum, Sedum aruum, Sedum quadrifida, Sedum integrefolia, Sedum telephium, Sedum algida, Sedum crenulata, Sedum pinnatifida, Sedum hybridum, Sedum aizoon, Sedum purpureum, Sedum heterodonta, Sedum viridula, Sedum kirilowii, Sedum linearifolia, Sedum gelida*, and *Sempervivum soboleferum*.

In one embodiment of the invention, the extract may be in tablet form.

The invention is also directed to a pharmaceutically acceptable composition comprising a standardized extract of a plant belonging to Crassulaceae comprising 2-(4-Hydroxyphenyl)ethyl-β-D-glucopyranoside or 3-[6-O-(α-L-arabinopyranosyl)-β-D-glucopyranosyl]-oxy-1-phenylpropene.

The pharmaceutically acceptable composition comprises a plant belonging to the genus *Sedum* and *Sempervivum*. And in particular, the plant may be *Sedum rosea, Sedum maximum, Sedum auglicum, Sedum aruum, Sedum quadrifida, Sedum integrefolia, Sedum telephium, Sedum algida, Sedum crenulata, Sedum pinnatifida, Sedum hybridum, Sedum aizoon, Sedum purpureum, Sedum heterodonta, Sedum viridula, Sedum kirilowii, Sedum linearifolia, Sedum gelida*, or *Sempervivum soboleferum*.

The invention is further directed to a pharmaceutically acceptable tablet comprising a composition which comprises an extract of a plant belonging to Crassulaceae comprising 2-(4-Hydroxyphenyl)ethyl-β-D-glucopyranoside or 3-[6-O-(α-L-arabinopyranosyl)-β-D-glucopyranosyl]oxy-1-phenylpropene.

The invention is also directed to a method for treating a symptom of depression comprising administering to a person in need thereof, a composition comprising 2-(4-Hydroxyphenyl)ethyl-β-D-glucopyranoside or 3-[6-O-(α-L-arabinopyranosyl)-β-D-glucopyranosyl]oxy-1-phenylpropene, and a pharmaceutically acceptable carrier thereof. The method is especially useful when the depression is mild to moderate.

In another embodiment, the invention is directed to a method for preparing a composition comprising an extract of Crassulaceae for treating a symptom of depression, which comprises:

a) dispersing plant matter of said Crassulaceae in an alcohol;

b) heating said dispersed plant matter, c) separating the alcohol solution from said plant matter, d) evaporating the alcohol solution to obtain spissum, e) dissolving the spissum in a liquid solution, f) extracting the liquid solution of step e) with a salt of an acid, g) extracting the liquid solution of step f) with an alcohol solution, and i) evaporating the alcohol solution of step g) to obtain said extract.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
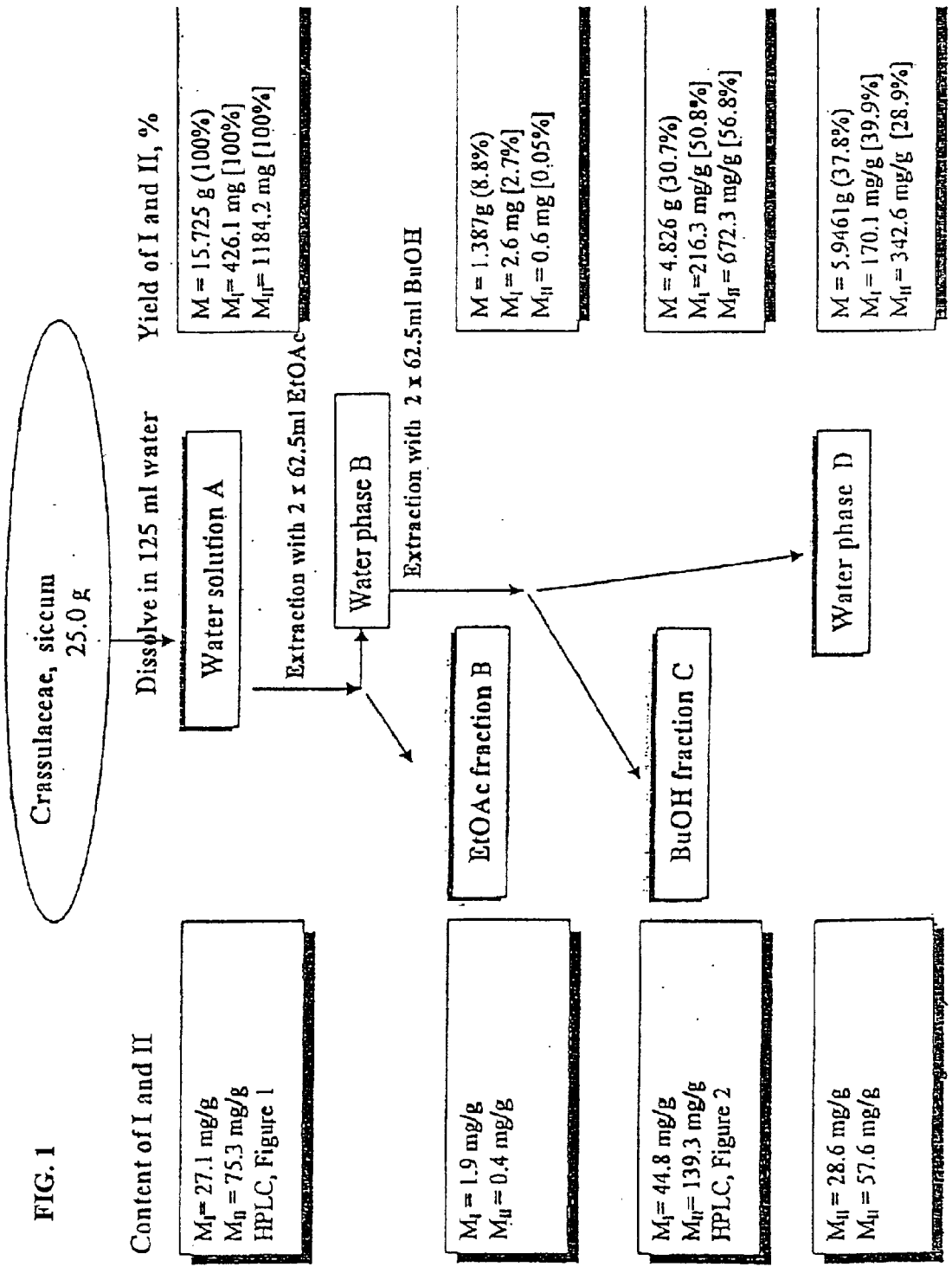
FIG. 1 shows a scheme for obtaining special extracts from Crassulaceae plant material.

The present invention is directed to antidepressants, more particularly to the special Crassulaceae extracts Carpediol containing 2-(4-hydroxyphenyl)ethyl-β-D-glucopyranoside (compound I) and 3-[6-O-(α-1-arabinopyranosyl)-β-D-glucopyranosyl]-oxy-1-phenylpropene (compound II), that have substantially no effect on the pharmacokinetics of other drugs if used concomitantly with Carpediol.

As used herein, "ASFC" refers to a fixed combination of *Acanthopanax senticosis* and *Schizandra chinensis* extracts.

As used herein, "HP" refers to *Hypericum perforatum* extract. "HPSE" refers to *Hypericum perforatum* special extract. And "HRFC" refers to a fixed combination of *Hypericum perforatum* and Crassulaceae extracts.

As used herein, "mild to moderate depression" means not very pronounced depression, and may be indicated by a score of less than or equal to 12, according to the Hamilton scale.

As used herein, "pharmacokinetics" means the time course of drug and metabolite levels in different fluids, tissues, and excreta of the body.

As used herein, "substantially" having no effect on the pharmacokinetics of a concomitantly administered medicine means that the difference is less than about 25% for three main pharmacokinetic parameters: total clearance, apparent volume of distribution, and area under the pharmacokinetic curve for the pure drug and that is concomitantly administered with other medicines.

As used herein, "insomnia" refers to difficulty in sleeping, or disturbed sleep patterns leaving the perception of insufficient sleep.

As used herein, "somatization" refers to a neurotic illness characterized by the presence of multiple pseudosomatic symptoms, including those seen in classic convulsion hysteria.

As used herein, "emotional instability" refers to a neurotic condition characterized by unprovoked irritability and frequent change in mood.

As used herein, "low self esteem" refers to neurotic depressive situation when a person underestimates his self-capabilities.

As used herein, "CRE" refers to Crassulaceae extract. "CRE-A" refers to a special extract of Crassulaceae. "CRE-B", "CRE-C", and "CRE-D" refer to specific types of Crassulaceae special extracts. A formulated form of the extract is also known as Carpediol.

By specific types of Crassulaceae family, it is meant those plants which contain the 2-(4-hydroxyphenyl)ethyl-β-D-glucopyranoside (compound I) and/or 3-[6-O-(α-1-arabinopyranosyl)-β-D-glucopyranosyl]-oxy-1-phenylpropene (compound II). In particular, the following species are included without limitation, *Sedum rosea, Sedum maximum, Sedum auglicum, Sedum aruum, Sedum quadrifida, Sedum integrefolia, Sedum telephium, Sedum algida, Sedum crenulata, Sedum pinnatifida, Sedum hybridum, Sedum aizoon, Sedum purpureum, Sedum heterodonta, Sedum viridula, Sedum kirilowii, Sedum linearifolia, Sedum gelida*, and *Sempervivum soboleferu*.

The composition of the invention may include a single extract from any one of a plant belonging to the family Crassulaceae, or the composition may include a combination of a plurality of the Crassulaceae plants. In one embodiment, the composition may comprise plants in the *Sedum* genus and in the *Sempervivum* genus.

With regard to the formulation of Carpediol, if desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, and so on.

The amount of the herbal medicine in a formulation can vary within the full range employed by those skilled in the art, e.g., from about 0.01 weight percent (wt %) to about 99.99 wt % of the medicine based on the total formulation and about 0.01 wt % to 99.99 wt % excipient.

The preferred mode of administration, for the conditions mentioned above, is oral administration using a convenient daily dosage regimen which can be adjusted according to the degree of the complaint. For said oral administration, a pharmaceutically acceptable, non-toxic composition is formed by the incorporation of the herbal composition in any of the currently used excipients, such as, for example, pharmaceutical grades of mannitol, lactose, starch, magnesium stearate, sodium saccharine, talc, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt % and 99.99 wt % of the active compound according to this invention.

In one embodiment, the compositions will have the form of a sugar coated pill or tablet and thus they will contain, along with the active ingredient, a diluent such as lactose, sucrose, dicalcium phosphate, and the like; a disintegrant such as starch or derivatives thereof; a lubricant such as magnesium stearate and the like; and a binder such as starch, polyvinylpyrrolidone, acacia gum, gelatin, cellulose and derivatives thereof, and the like.

It is understood that by "pharmaceutical composition" or "herbal medicinal composition", it is meant that the herbal composition is formulated into a substance that is to be administered purposefully for treating or preventing mild to moderate depression, as well as symptoms of depression, in an individual.

In an embodiment of the invention, special extracts of Crassulaceae, Carpediol is administered to a person suffering from mild depression to treat symptoms of depression. A significant advantage of using Carpediol is that it does not interfere negatively with the pharmacokinetic activity of other medications. For instance, serum levels of a concomitantly administered drug remained at or about the same level in the Carpediol administered samples, as the level found in the serum of placebo administered samples. Moreover, clinical tests show the effectiveness of Carpediol extracts in treating mild depression.

The following examples are offered by way of illustration of the present invention, and not by way of limitation.

EXAMPLES

Example 1

Preparation of Carpediol Extracts: CRE-A, CRE-B, CRE-C, and CRE-D

Carpediol extract may be prepared by the following exemplified method:
a) Extracting a plant material from the Crassulaceae family by a hydro-alcoholic solvent. Typically, the solvent is an ethanol/water mixture ranging from 1% ethanol to 99% ethanol. Other alcohols, such as methanol and butanol may be used. Preferably, the extraction process is a specific validated process that meets the Good Manufacturing Practice standards of U.S. Food and Drug Administration. The temperature of the extraction procedure can be in a range between 20° C. to 95° C. depending on length of extraction time and quality of the raw material.
b) Separating the extraction solvent from the plant material.
c) Evaporating alcohol to obtain a soft material, so called spissum which contains Carpediol, and which contains about 0.8% to about 2.5% 2-(4-hydroxyphenyl)ethyl-β-D-glucopyranoside, and about 1.5% to about 4.5% 3-[6-O-(α-L-arabinopyranosyl)-β-D-glucopyranosyl]-oxy-1-phenylpropene.
d) Dissolving the spissum extract in water, thus yielding CRE-A. Preferably, the amount of water volume is about 1 to about 5 volumetric parts.
e) Extracting CRE-A with a solvent of ethylacetate saturated with water. Preferably, the amount of the composition of the solvent is approximately equal volume of ethylacetate saturated with water. Lighter (upper) ethylacetate phase comprises CRE-B.
f) Extracting the heavier (lower) water-phase in e) above with butanol, preferably in approximately equal volumes, to obtain CRE-C. The remaining water-phase is called CRE-D.
g) Analyzing an aliquot of CRE-A, CRE-B, CRE-C and CRE-D by HPLC and TLC.
h) Evaporating fractions CRE-A, CRE-B, CRE-C and CRE-D in section g) above to dryness. The residues are later dissolved in water for fractions CRE-A, CRE-C and CRE-D, and about 0.3% solution of carboxymethylcellulose in about 0.1% DMSO for water insoluble fraction CRE-B, to obtain stock solutions of about 50 mg/ml.
i) Diluting stock solutions of CRE-A, CRE-C and CRE-D with water, and stock solution of CRE-B with about 0.3% solution of carboxymethylcellulose in about 0.1% DMSO to obtain test solutions of CRE-A, CRE-B, CRE-C and CRE-D in concentrations of about 10 mg/ml, 5 mg/ml and 2.5 mg/ml, respectively.

Example 2

Method of Analysis of Carpediol

Thin Layer Chromatography (TLC): $R_f$–0.08

| | |
|---|---|
| Solvent system: | Chloroform-Methanol, 6:1 |
| Spotting size: | 20 µl |
| Samples: | 1) Standard mixture of reference standards (RS)-compound I and compound II, 0.3:0.3 mg/ml |
| | 2) Water Solution A, 50 mg/ml |
| | 3) EtOAc fraction B, 50 mg/ml |
| | 4) BuOH fraction C, 50 mg/ml |
| | 5) Water phase D, 50 mg/ml |
| Detection: | a) UV-254; |
| | b) Komarovski reagent: 1 ml of 50% ethanolic sulfuric acid and 10 ml of 2% methanolic parabenzaldehyde are mixed shortly before use, heated at 100° C. for 3–5 min. Observe the size and intensity of cineol spot ($R_f$~0.4). |

High Performance Liquid Chromatography (HPLC):

Reagents and analytical standards:

Internal standard (IS)-4-hydroxybenzoic acid-ethyl ester by Aldrich Chemical Company, 2-(4-Hydroxyphenyl)ethyl-β-D-glucopyranoside (compound I) was supplied by Swedish Herbal Institute, and 3-[6-O-(α-L-Arabinopyranosyl)-β-D-glucopyranosyl]-oxy-1-phenylpropene (compound II) was isolated and identified as described in Zapesochnaya et al. (Khim. Prir. Soedin.,1982, 18, 723; Chem. Nat. Compd. (Engl. Transl.),1982, 18, 685).

2-(4-Hydroxyphenyl)ethyl-β-D-glucopyranoside

Relative retention time $R_S = R_{compound\ I}/R_{IS}$ = 3.5 min/16.2 min = 0.22

Mass-spectra (EI 70 eV) of acetate, m/z: 331 (Glc), 169, 163, 162, 121, 120 (100%), 109, 91, 43.

Mass-spectra (EI 70 eV) of trimethylsilyl (TMS) ether, m/z: 437, 407, 381, 361, 305, 267, 231, 217, 204 ($M^+$-Glc, 100%), 193, 192, 177, 147, 103, 73.

3-[6-O-(α-L-Arabinopyranosyl)-β-D-glucopyranosyl]-oxy-1-phenylpropene

Synonym(s): Cinnamyl alcohol β-vicianoside, 3-Phenyl-2-propen-1-ol O-[α-L-arabinopyranosyl-(1->6)-β-D-glucopyranoside]$C_{20}H_{28}O_{10}$, MW 428.4 M.p. 171–173° C. (from EtOH) $[\alpha]^{20}_D$ –56.5° (c 0.7, $CHCl_3$-MeOH, 1:1)

UV, ethanol, $\lambda_{max}$: 252 nm (log ε4.28, $A^{1\%}$ cm 460).

Relative retention time $R_S = R_{compound\ II}/R_{IS}$ = 9.2 min/16.2 min = 0.57

Mass-spectra (EI 70 eV) of acetate, m/z: 331, 169, 152, 139, 127, 117 ($M^+$-Ara-Glc, 100%), 115, 109, 97, 91, 43.

Mass-spectra (EI 70 eV) of trimethylsilyl (TMS) ether, m/z: 495, 451(Glc), 379, 361, 349(Ara), 305, 259 (100%), 217, 204, 191, 169, 147, 117 ($M^+$-Ara-Glc, 100%), 73.

TABLE 1

$^1$H-NMR, $^{13}$C-NMR, COSY, TOCSY, NOESY and hmqc spectra

| Fragment | Carbone No | δ $^{13}$C, ppm | δ $^1$H, ppm | Coupling constants-J, Hz |
|---|---|---|---|---|
| Aglycone | 1 | 67.87 | 1a 4.23 | J(7a,7b) = 13.3; J(7a,8) = 6.4 |
| | | | 1b 4.42 | J(7b,8) = 5.4 |
| | 2 | 126.92 | 6.70 | J(8,9) = 15.8 |

TABLE 1-continued $^1$H-NMR, $^{13}$C-NMR, COSY, TOCSY, NOESY and hmqc spectra

| Fragment | Carbone No | δ $^{13}$C, ppm | | δ $^1$H, ppm | Coupling constants-J, Hz |
|---|---|---|---|---|---|
| | 3 | 130.87 | | 6.68 | |
| | 4 | 135.86 | | — | |
| | 5, 9 | 125.68 | | 7.44 | J(11,12) = 7.0; J(11,13) = 1.75 |
| | 6, 8 | 127.95 | | 7.35 | J(12,13) = 7.2 |
| | 7 | 127.95 | | 7.24 | |
| Glc | 1' | 101.30 | | 4.23 | |
| | 2' | 72.83 | | 3.01 | J(1',2') = 7.6; J(2',3') = 8.75; J(2'OH) = 4.7 |
| | 3' | 76.05 | | 3.16 | J(3',4') = 8.7–9.0; J(3'OH) = 4.4 |
| | 4' | 69.97 | | 3.37 | J(4',5') = 7.4; J(4'OH) = 5.0 |
| | 5' | 75.09 | | 3.20 | |
| | 6' | 67.55 | 6'a | 3.55 | J(6'a,5') = 6.6; J(6'a,6'b) = 11.4 |
| | | | 6'b | 3.95 | J(6'b,5') = 1.9 |
| Ara | 1" | 102.87 | | 4.25 | J(1",2") = 5.8 |
| | 2" | 69.63 | | 3.08 | J(2",3") = 9.3; J(2".OH) = 4.7 |
| | 3" | 71.94 | | 3.31 | J(3",4") < 5 |
| | 4" | 66.71 | | 3.64 | J(4",5"a) = 3.5; J(4",5"b) = 1.9; J(4"OH) = 4.2 |
| | 5" | 64.25 | 5"a | 3.67 | J(5"a,5"b) = 11.5; J(5"a,4") = 3.5 |
| | | | 5"b | 3.30 | J(5"b,4) = 1.9 |

* "Varian" Mercury NMR spectrometer, 300 MHz for protons; solvent-[$^2$H]$_6$-DMSO; 30° C.

Chromatographic System. Beckman GOLD HPLC system consisting of: Double pump Programmable Solvent Module mod. 125; Single channel UV detector module mod. 166; PS/1 Computer 486 DX-33 with management software supplied by Beckman; Epson FX—800 printer: Column: LiChroCART 125-4 with Lichrospher 100 RP-18, 125×4 mm, 5 μm (Merck); Precolumn LiChroCART 4-4 with Lichrospher 100 RP-18 (5 μm). Injection valve: Rheodyne mod. 7725I with 20 μl loop.

Chromatographic Conditions

| Mobile phase | |
|---|---|
| Solution A: | water-1% (v/v) 0.1N phosphoric acid |
| Solution B: | acetonitrile-1% (v/v) 0.1N phosphoric acid |
| Gradient: | Start 10% B |
| | 00–05 min, 10%–20% |
| | 05–20 min, 20%–40% |
| Post run | 20–21 min, 40%–10% |
| | 21–25 min, 10% |
| Flow: | 1.0 ml/min |
| Injection volume: | 20 μl |
| Detection: | 00–06 min, UV = 221 nm |
| | 06–20 min, UV = 252 nm |
| Samples: | 1) Standard mixture of reference standards (RS)-compound I:compound II:IS, 0.1:0.1:0.025 mg/ml |
| | 2) Water Solution A, 50 mg/ml |
| | 3) EtOAc fraction B, 50 mg/ml |
| | 4) BuOH fraction C, 50 mg/ml |
| | 5) Water phase D, 50 mg/ml |

Calculations $$M_I = m_c \cdot \frac{S_I}{S_c \cdot W} \cdot \frac{1}{k10}$$

$M_I$—the amount of compound I in 1.0 g of Carpediol extract, siccum, mg $m_c$—sample weight of IS, mg (=50)

$S_I$—peak area of compound I on the chromatogram of the analytical sample (AS)

$S_c$—peak area of the IS on the chromatogram of AS

W—the sample weight of compound I extract siccum, g

10—dilution factor of IS k—detection coefficient (0.14) calculated using chromatogram of RS as follows:

$$K = \frac{C_m S}{C S_m}$$

C—concentration of IS in RS (0.025 mg/ml)

$C_m$—concentration of compound I in RS (0.1 mg/ml)

S—peak area of compound I on the chromatogram of RS $S_m$—peak area of IS on the chromatogram of RS.

$$M_{II} = m_c \cdot \frac{S_{II}}{S_c \cdot W} \cdot \frac{1}{k10}$$

$M_{II}$—the amount of compound II in 1.0 g of Carpediol extract siccum, mg $m_c$—sample weight of IS, mg (=50)

$S_{II}$—peak area of compound II on the chromatogram of AS $S_c$—peak area of the IS on the chromatogram of AS W—the sample weight of compound II extract siccum, g 10—dilution factor of IS k—detection coefficient (0.359) calculated using chromatogram of RS as follows:

$$K = \frac{C_m S}{C S_m}$$

C—concentration of IS in RS (0.025 mg/ml);

$C_m$—concentration of compound II in RS (0.1 mg/ml);

S—peak area of compound II on the chromatogram of RS;

$S_m$—peak area of IS on the chromatogram of RS.

Example 3

Antidepressant Activity of CRE in Behavioral Despair "Forced Swimming" Test

Behavioral despair was proposed as a model to test for antidepressant activity by Porsolt et al (25–27). It was suggested that mice or rats forced to swim in a restricted space from which they cannot escape are induced to a characteristic behavior of immobility. This behavior reflects a state of despair which can be reduced by several agents which are therapeutically effective in human depression.

Procedure—The procedure described by Porsolt et al. (25–27) was used with minor modifications described by Chatterjee et al. (28–29). Male Wistar rats weighing 170–200 g were used. They were brought to the laboratory at least one day before the experiment and were housed separately in cages with free access to food and water. Naive rats were individually forced to swim inside a vertical glass cylinder (height: 50 cm; diameter: 25 cm, containing 20 cm of water maintained at 25° C.). Rats placed in the cylinders for the first time were initially highly active, vigorously swimming in circles, trying to climb the wall or diving to the bottom. After 2–3 minutes, activity began to subside and to be interspersed with phases of immobility or floating of increasing length. After 5–6 minutes, immobility reached a plateau where the rats remained immobile for approximately 80% of the time. After 15 minutes in the water, the rats were removed and allowed to dry in a heated enclosure (32° C.) before being returned to their home cages. Total immobility time, i.e., the time of complete cessation of swimming with the head floating just above water level, was quantified 48 hours later after re-exposing them to the water for 5 minutes. They were placed in the cylinder 48 hours later and the total duration of immobility was measured during a 5 minute test. Floating behavior during this 5 minute period has been found to be reproducible in different groups of rats. An animal was judged to be immobile whenever it remained floating passively in the water in a slightly hunched but upright position, its nose just above the surface. Test samples (*Hypericum* extracts: HP, HPSE, Jarsin 300, HRFC, Crassulaceae special extracts, Carpediol) and standard drugs (amitriptyline and Imipramine) were administered 3 times immediately after pre-exposure, and 24 and one hour prior to testing (re-exposure) as described in Chatterjee et al., Antidepressant activity of *Hypericum perforatum* and Hyperforin: the neglected possibility. Pharmacopsychiatry. 31 (Suppl 1):7–15 1998), which is incorporated by reference herein in its entirety.

Evaluation—Duration of immobility was measured in controls and animals treated with various doses of a test drug or standard. Antidepressant drugs, but also stimulants like amphetamine and caffeine, reduced duration of immobility. Dose-responses were evaluated.

Critical Assessment of the Method—Advantages of the method are the relative simplicity, and the fact that no interaction with other drugs is necessary. Like in other behavioral tests, e.g. the catalepsy test in chicken, not only antidepressants and monoamino-oxidase inhibitors but also central stimulants give positive results. Despair swim test has been used for evaluation of efficiency of *Hypericum* extracts (28–30).

Experimental—We used this test for evaluation of antidepressant activity of Carpediol extract (CRE), Carpediol special extracts CRE-B, CRE-C, CRE-D, fixed combination of *Acanthopanax senticosus* and *Schizandra chinensis* extracts, 2:1 (ASFC), *Hypericum perforatum* extract (HP) *Hypericum perforatum* special extract (HPSE), its fixed combination (1:1, w/w) with Crassulaceae extract (HRFC) and compared their activity with known antidepressive drugs (imipramine and amitriptyline) and a widely used Hypericum Drug—Jarsin300 (Lichwere Pharma, FRG, Batch No 96021102, Exp January 1999).

Two series of experiments were performed with the following test drugs:

Series A: HP, HPSE, HRFC, CRE, Jarsin, amitriptyline.
Series B: CRE-A, CRE-B, CRE-C, CRE-D, ASFC, imipramine.

Animals: Male Wistar strain rats (170–200 g) were obtained from the Central Animal House of the Institute of Fine Organic Chemistry of the National Academy of Sciences, Yerevan, Armenia. They were group-housed, four per cage at ambient temperature of 20±2° and 40–50% relative humidity, with a 12 hour dark/12 hour light cycle (lighting on time 8 a.m.). The animals had free access to pellet chow (Comby) and drinking water.

Drugs and Vehicles of Administration

Series A

An alcoholic Hypericum extract (HP) containing about 1% hyperforin, HPSE containing about 10% hyperforin, HRFC containing about 5% hyperforin, Jarsin300 (Lichtwer Pharma, FRG) containing about 1% hyperforin, HRFC, and CRE, each were suspended in 0.3% carboxymethylcellulose in 1% DMSO and administered in a volume of 5 ml/kg (per os). The extracts were administered once daily for 3 consecutive days. Experiments were performed on day 3, 1 hour after the last drug or vehicle application. Amitriptyline was used as the standard antidepressant, and was administered in a single dose of 3 mg/kg (p.o.) with a pretreatment time of 30 min.

Series B

Preparation of CRE test solutions A-D in concentrations of 10 mg/ml, 5 mg/ml and 2.5 mg/ml is described in Example 1. They were administered in a volume of 5 ml/kg (p.o.). The extracts were administered once daily for 3 consecutive days. Experiments were performed on day 3, 1 hour after the last drug or vehicle application. Imipramine-HCl diluted with water to concentration of 6 mg/ml, positive control was used as the standard antidepressant. Imipramine was administered in a single dose of 30 mg/kg (p.o.) with a pretreatment time of 30 minutes. All behavioral studies were performed between 1–3 p.m. and recorded by a video camera. The tapes were evaluated afterwards by an observer who was not informed about the type of treatment each animal had received.

Statistics—Statistical analysis of the duration of immobilization time of rats in swimming test was performed by unpaired two tailed Students t-test with significance 95% confidence interval. All data were expressed as a mean±SEM, standard deviation and variation coefficient. Data management and calculations of mean values were performed using PRISM Statistical Software Version 2.01, 1996.

Figure 2:
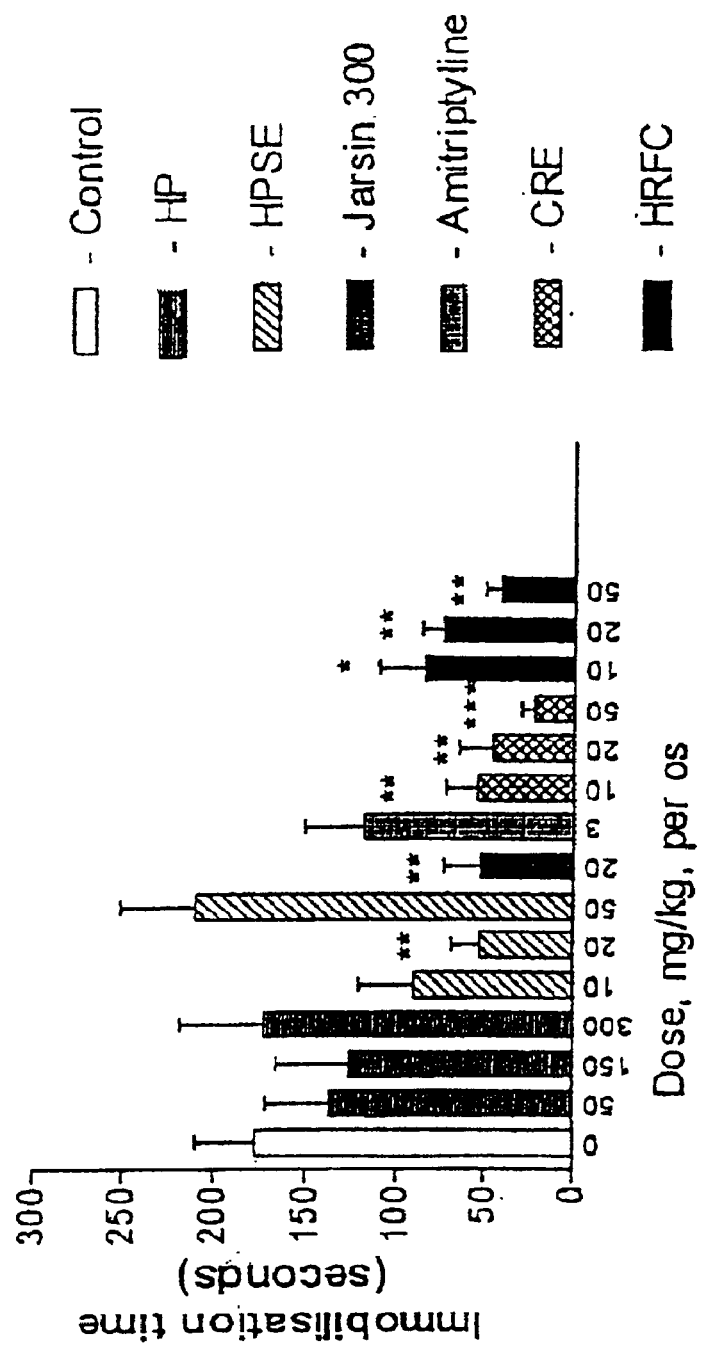
FIG. 2 shows the effect of Amitriptyline, Hypericum extracts (HP, HPSE and Jarsin300), Carpediol, and their fixed combination (HRFC-Hypericum and Carpediol, 1:1) in "behavioral despair" test (data are means±SEM) in rats. The observed effects marked * represent statistically significant differences from the control group. *, , and * indicate $p<0.005$, $<0.001$ and $<0.0001$, respectively.
Figure 3:
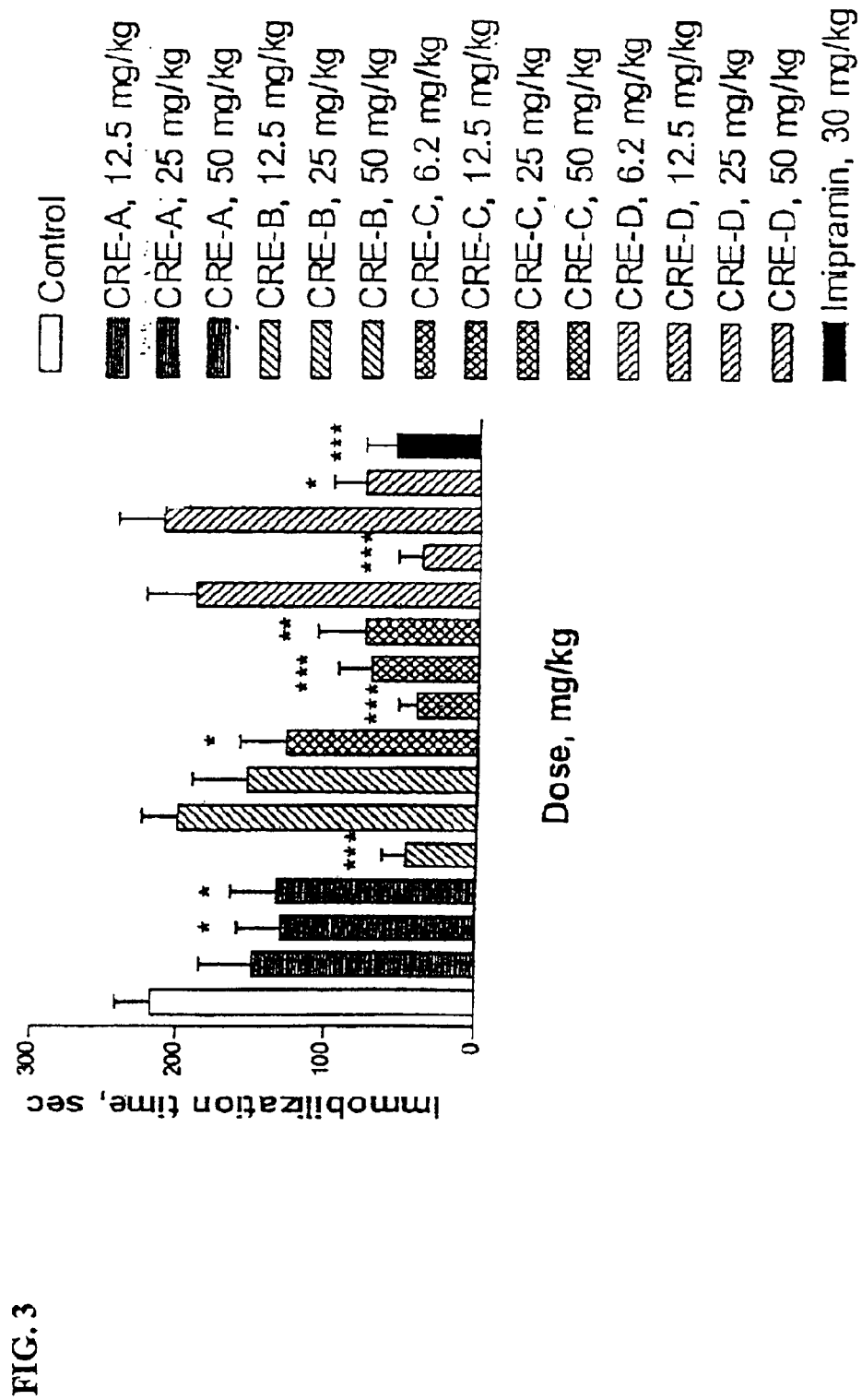
FIG. 3 shows the effects of Carpediol and Imipramine in "behavioral despair" test (data are means±SEM) in rats.

Results—Table 2 and FIG. 2 show the results of Series A experiment: CRE is more active than Hypericum extracts alone as well as its fixed combination of CRE-HRFC. Table 3 and FIG. 3 show the results of Series B experiments. The most active was CRE-C, which recorded the highest content of compound II. The most effective composition was 12.5 mg/kg of CRE-C.

TABLE 2

Effect of Amitriptyline, Hypericum, and Carpediol, in "Behavioral Despair" Test

| Test article (mg/kg, route of administration) | Duration of immobility (seconds) | Percent | Percent decrease |
|---|---|---|---|
| Vehicle | 177.6 ± 32.19, n = 8 | 100.0 | 0 |
| HP (50, p.o.) | 137.1 ± 35.11, n = 8 | 77.2 | 22.8 |
| HP (150, p.o.) | 125.8 ± 40.29, n = 6 | 70.8 | 29.2 |
| HP (300, p.o.) | 173.3 ± 44.95, n = 6 | 99.8 | 0.2 |
| HPSE (10, p.o.) | 90.13 ± 30.54, n = 8 | 50.7 | 49.3 |
| HPSE (20, p.o.) | 52.69 ± 16.47*, n = 8 | 29.7* | 70.3* |
| HPSE (50, p.o.) | 210.5 ± 40.78, n = 6 | 118.5 | −18.5 |
| Jarsin 300 (20, p.o.) | 52.13 ± 21.29*, n = 8 | 29.4* | 70.6* |
| Amitriptyline (3, p.o.) | 117.8 ± 33.32, n = 8 | 66.3 | 43.7 |
| CRE (10, p.o.) | 54.0 ± 18.77**, n = 8 | 30.4** | 69.6** |
| CRE (20, p.o.) | 46.13 ± 19.40**, n = 8 | 26.0** | 74.0** |
| CRE (50, p.o.) | 22.54 ± 6.96***, n = 7 | 12.7*** | 87.3*** |
| HRFC (10, p.o.) | 85.43 ± 25.22*, n = 7 | 48.1* | 51.9* |
| HRFC (20, p.o.) | 74.75 ± 12.08**, n = 8 | 42.1** | 57.9** |
| HRFC (50, p.o.) | 41.88 ± 8.46**, n = 8 | 23.6** | 76.4** |

Superscripts *, , and * indicate $P < 0.05$, $< 0.01$ and $< 0.001$, respectively different from vehicle treated controls (Student's unpaired t-test). Data are means ± SEM in rats.

TABLE 3

Effect of CRE-A, CRE-B, CRE-C, CRE-D, Imipramine and ASFC in "Behavioral Despair" Test

| Test article (mg/kg, route of administration) | Duration of immobility, Seconds | Percent | Percent decrease |
|---|---|---|---|
| Vehicle | 217.5 ± 24.1, n = 8 | 100.0 | 0 |
| CRE-A (12.5 p.o.) | 149.1 ± 35.5, n = 8 | 68.5 | 31.5 |
| CRE-A (25 p.o.) | 130.4 ± 29.0*, n = 8 | 60.1* | 39.9* |
| CRE-A (50 p.o.) | 133.3 ± 30.6*, n = 8 | 61.3* | 38.7* |
| CRE-B (12.5 p.o.) | 54.6 ± 15.6***, n = 7 | 25.1*** | 74.9*** |
| CRE-B (25 p.o.) | 200.6 ± 24.8, n = 8 | 92.2 | 7.8 |
| CRE-B (50 p.o.) | 154.1 ± 37.0, n = 8 | 70.8 | 29.2 |
| CRE-C (6.25 p.o.) | 160.3 ± 30.4, n = 7 | 73.6 | 26.4 |
| CRE-C (12.5 p.o.) | 41.5 ± 12.1***, n = 8 | 19.1*** | 80.9*** |
| CRE-C (25 p.o.) | 71.6 ± 22.6***, n = 8 | 32.9*** | 67.1*** |
| CRE-C (50 p.o.) | 101.8 ± 36.6**, n = 6 | 46.8** | 53.2** |
| CRE-D (6.25 p.o.) | 190.4 ± 34.2, n = 8 | 87.5 | 12.5 |
| CRE-D (12.5 p.o.) | 39.1 ± 15.7***, n = 8 | 18.0*** | 92.0*** |
| CRE-D (25 p.o.) | 212.9 ± 31.0, n = 8 | 97.8 | 2.2 |
| CRE-D (50 p.o.) | 88.1 ± 20.5***, n = 7 | 40.5*** | 59.5*** |
| ASFC (12.5 p.o.) | 215.5 ± 29.8, n = 8 | 99.1 | 0.9 |
| ASFC (25 p.o.) | 118.0 ± 26.2*, n = 8 | 54.2* | 45.8* |
| ASFC (50 p.o.) | 182.6 ± 21.7, n = 8 | 83.9 | 16.1 |
| Imipramine (30 p.o.) | 76.0 ± 21.1***, n = 6 | 34.9*** | 65.1*** |

Superscripts *, , and * indicate $P < 0.05$, $< 0.01$ and $< 0.001$, respectively different from vehicle treated controls (Student's unpaired t-test). Data are means ± SEM in rats.

Example 4

Effect of Carpediol Extract on the Pharmacokinetics of Theophylline in Rats: Comparative Study with *Hypericum perforatum* (Jarsin 300)

Example 3 showed that Carpediol is more active than the most active *Hypericum* extracts (Jarsin 300 and other extracts with high content of hyperforine) and imipramine in behaviour despair (the forced swimming) test. The aim of Example 4 is to verify whether Carpediol has any effect on the pharmacokinetics of theophylline which can decrease its therapeutic effect. Theophylline (1,3-dimethylxantin) is a widely used bronchodilator. Different salts of theophylline exist in various dosage forms. Most frequently used is ethylenediamine salt with brand names Euphylline and Aminophylline containing 85% of theophylline. The pharmacokinetics of theophylline is well studied. Only 13% of theophylline is eliminated with urine while a major portion is metabolized (31). The elimination rate and clearance of theophylline depends upon many factors that activate or inhibit enzymatic systems of the liver, particularly with simultaneous applications of other drugs. Thus, erythromycin, propranolol and cimetidine inhibit, and phenobarbital activates, the metabolism of theophylline (32, 33). It was recently found that *Hypericum* extracts also activate the metabolism of theophylline (34). This can decrease the concentration of theophylline in blood lower than required to reveal an efficient therapeutic effect (31,34).

A comparative study of the effects of Carpediol and *Hypericum* on the pharmacokinetics of theophylline in rats is described below.

Materials and Methods

Extracts and Other Substances:

(a) Carpediol special extract CRE-C was prepared from Extr. Carpediol spissum (Batch No Ex 20404); Swedish Herbal Institute, Gothenburg, Sweden) as described above in Example 1. The content of 2-(4-hydroxyphenyl)ethyl-β-D-glucopyranoside, and 3-[6-O-(α-L-arabinopyranosyl)-β-D-glucopyranosyl]-oxy-1-phenylpropen in the dry extract were 44.8 mg/g and 139.3 mg/g, respectively.

(b) Jarsin300 (Lichwere Pharma, FRG) containing about 1% hyperforin and 0.1% hypericin and pseudohypericin per dosage was obtained from Lichwere Pharma, FRG.

(c) A 2.4% solution of "Euphyllini pro injectionibus" Aminophylline containing 80% theophylline and 20% ethylenediamine was supplied by Darnitsa Co. (Ukraine).

(d) The reference standard of theophylline anhydrous ethylenediamine was obtained from Glaxo Welcome. It was analyzed for purity by HPLC, Capillary electrophoresis, $^{1}$H-NMR and $^{13}$C-NMR.

(e) Internal standard: Methyl-4-hydroxybenzoate 99%, F.W. 152.15 Aldrich.

(f) Water, demonized and distilled.

(g) Water for High Performance Capillary Electrophoresis (HPCE), HEWLETT-PACKARD.

(h) Buffer pH=9.3 for HPCE (50 mM Borate).

(i) 0.1N Sodium Hydroxide Solution for HPCE.

(j) Chloroform HPLC grade.

(k) 2-Propanol spectrophotometric grade.

(l) Methanol Chromasorv.

Animals—In this study, 144 time-mated male Wistar rats were used. Breeder: Institute of Fine Organic Chemistry of the National Academy of Science, Yerevan. The initial weight of the animals: 130–170 g (mean weight 149.93±12.4 g). The animals were kept in the animal room for 10–15 days prior to the start of the study under a 12/12 hour light/dark cycle and had free access to standard rat chow. All animals were clinically examined upon arrival and any animal showing signs of abnormality or disease was excluded. Animals considered unsuitable for the study were replaced before the start. No animal was replaced following the start of the study.

Food—A standardized diet for rats served as food. Feeding was discontinued before administration of test substance. Only tap water was offered ad lib.

Caging—During the observation period the female animals were kept separately in 55×35×25 cm cages (polystyrol case and lattice framed steel lid). Wood sawdust was used as bedding in the cages.

Room environment—Temperature and humidity was regularly monitored. Target ranges for temperature and relative humidity was 22° C.±4° C. and 40%±5% respectively, and there were 1–2 air changes per hour. Light regiment: 12 hours light-12 hours darkness.

Room and cage sanitation—Each day or after completion of all work, floors were swept and then mopped with an amphoteric biocide/cleanser. Excretions were collected on a tray lined with absorbent paper suspended beneath each cage every second day.

Dosage and Administration—An appropriate amount of herbal extract was dissolved in distilled water and given at 10:00–10:30 am by oral gavage. Suspensions were shaken gently before oral administration. Suspensions were prepared fresh every day. Control animals were given an appropriate volume of drinking water. Blood samples from rats receiving the carrier only were also analyzed. The study design is shown in Table 4.

TABLE 4

Design of the Study

| Group No. | Total number of animals | Number of animals per time point in each group | Co-administered drug | Daily dose (mg/kg/day) | Administered volume ml/kg | Duration of pretreatment (days) | Blood sampling time after infusion of theophylline, (hours) |
|---|---|---|---|---|---|---|---|
| 1 | 48 | 6 | Control (water) | 0 | 10 | 3 | 0; 0.25; 0.5; 1.0; 2.0; 4.0; 6.0; 8.0 |
| 2 | 48 | 6 | CRE-D | 25 | 10 | 3 | 0; 0.25; 0.5; 1.0; 2.0; 4.0; 6.0; 8.0 |
| 3 | 48 | 6 | Jarsin300 | 300 | 10 | 3 | 0; 0.25; 0.5; 1.0; 2.0; 4.0; 6.0; 8.0 |

Group No 1.

Groups of six animals were treated orally with water (10 ml×2 times per day) for three days. 60 minutes after last administration of water, a solution of Aminophylline (10 ml/kg) was given to each animal in dose of 240 mg/kg (corresponding to 192 mg/kg of Theophylline) and blood samples were taken 0.25, 0.5, 1.0, 2.0, 4.0, 6.0 and 8.0 hours after the theophylline administration. A separate group of animals was used for each time point.

Group No 2.

Preparation of Carpediol special extract CRE-C test solution in concentrations of 2.5 mg/ml is described in Example 1. It was administered orally in a volume of 10 ml/kg of body weight. Freshly prepared extract was administered two times daily for 3 consecutive days. Single dose—25 mg/kg, daily dose—50 mg/kg. 60 minutes after last administration, a water solution of Aminophylline (10 ml/kg) was given to each animal in dose of 240 mg/kg (corresponding to 192 mg/kg of Theophylline) and blood samples were taken 0.25, 0.5, 1.0, 2.0, 4.0, 6.0 and 8.0 hours after the theophylline administration. A separate group of animals was used for each time point.

Group No 3.

One tablet of Jarsin 300 was suspended in 10 ml of water and administered two times daily for 3 consecutive days. 60 minutes after last administration, water solution of Aminophylline (10 ml/kg) was given to each animal in dose of 240 mg/kg (corresponding to 192 mg/kg of Theophylline) and blood samples were taken 0.25, 0.5, 1.0, 2.0, 4.0, 6.0 and 8.0 hours after the theophylline administration. A separate group of animals was used for each time point.

Sampling of blood and sample preparation—Animals were sacrificed by laboratory guillotine. Following decapitation, blood was collected separately in centrifuge tubes and centrifuged at 3000 rpm for 10 min. Blood serum was separated and 50 µl was taken for theophylline assay. Conservation of the samples: the centrifuge tubes were closed with caps, frozen and stored in a freezer for 1–3 days prior to bio-assay.

Analytical Method: Capillary Electrophoresis—A modified capillary electrophoresis method was used, using an internal standard and as a mobile phase 50 mM borate buffer (pH 9.3) without SDS.

Pre-assay preparation—The Ramzan et al. method (52) of extraction of theophylline from serum was modified as follows. 50 µl of blood serum was added to 10 µl of an internal standard methanol solution (methyl-paraben, 60 µg/ml) in centrifuge tube to obtain final concentration of methyl paraben 10 µg/ml. The solution was vortexed vigorously for 10 sec and 1 ml of solvent system of isopropanol and chloroform in a 5:95 ratio was added for extraction. The mixture was vortexed for 15 seconds and two layers were separated at 4° C. by centrifugation at 3000 rpm. Organic (lower) phase was removed, filtered if necessary and evaporated to dryness in a stream of nitrogen gas. The residue was dissolved in 300 µl of methanol and used fresh for injection to HPCE. Samples were analyzed by HP Capillary Electrophoresis System.

Statistical analysis—Statistical analysis was performed using GraphPad PRISM software, version 2.0, 1996, GraphPad Software, Inc. USA.

Pharmacokinetic parameters—The following model of independent pharmacokinetic parameters was calculated using the TOPFIT, version 1.1 (Godecke AG/Schering AG/Thomae GmbH) program.

Results

Pharmacokinetics of theophylline in rats—Theophylline is rapidly absorbed in the blood. Maximal concentration in serum is 176.7 µg/ml 60 minutes after drug administration. Then the level of theophylline decreased exponentially, and after 480 minutes was about 51 µg/ml (Table 5 and FIG. 4). The main pharmacokinetic parameters are shown in Tables 6 and 7.

TABLE 5

Concentration (mg/l) of Theophylline in Rat Serum (Group No. 1) After Oral Administration of Aminophylline

| Series, No | Time (min), after oral administration | | | | | | |
|---|---|---|---|---|---|---|---|
| | 15 | 30 | 60 | 120 | 240 | 360 | 480 |
| 1 | 153.35 | 143.18 | 154.77 | 61.23 | 61.03 | 77.92 | 44.98 |
| 2 | 146.67 | 337.56 | 231.79 | 97.22 | 105.31 | 81.94 | 89.99 |
| 3 | 101.82 | 101.83 | 86.37 | 56.61 | 169.15 | 31.38 | 16.09 |
| 4 | 181.11 | 135.41 | 138.11 | 96.28 | 77.66 | 43.95 | 22.05 |
| 5 | 172.059 | 89.49 | 194.27 | 57.30 | 94.86 | 42.46 | 69.25 |
| 6 | 225.306 | 50.10 | 255.06 | 71.98 | 114.84 | 73.58 | 63.68 |
| Mean | 163.4 | 142.9 | 176.7 | 73.44 | 103.8 | 58.54 | 51.01 |
| SD | 40.97 | 101.1 | 62.63 | 18.88 | 37.38 | 21.72 | 28.66 |
| SE | 16.73 | 41.27 | 25.57 | 7.707 | 15.26 | 8.867 | 11.70 |
| CV (%) | 25.08 | 70.73 | 35.44 | 25.71 | 36.01 | 37.01 | 56.19 |

Dose of Theophylline was 192 mg/kg. Mean weight of rats was 149.9 g.

TABLE 6

Model-Independent Pharmacokinetic Parameters of Theophylline (Group 1)

| Series No | $C_{max}$ (µg/ml) | $K_{el}$ (h$^{-1}$) | $t_{1/2}$ (h) | MRT (h) | $AUC_{0-\infty}$ (µm · h/ml) | $Cl_t$ (ml/min) | $V_d$ (l) |
|---|---|---|---|---|---|---|---|
| 1 | 153.4 | 0.1311 | 5.287 | 7.784 | 970.7 | 0.4945 | 0.2263 |
| 2 | 337.6 | 0.1539 | 4.504 | 6.835 | 1390 | 0.3453 | 0.1346 |
| 3 | 101.8 | 0.2044 | 3.391 | 4.830 | 745.4 | 0.6439 | 0.189 |
| 4 | 181.1 | 0.237 | 2.924 | 4.265 | 715.5 | 0.671 | 0.1698 |
| 5 | 172.1 | 0.117 | 5.940 | 8.626 | 1087 | 0.441 | 0.227 |
| 6 | 225.3 | 0.1393 | 4.977 | 7.396 | 1237 | 0.3881 | 0.1672 |
| Mean | 195.2 | 0.1638 | 4.504 | 6.623 | 1024 | 0.4973 | 0.1857 |
| SD | 80.48 | 0.0468 | 1.152 | 1.719 | 267.9 | 0.1341 | 0.0363 |
| SE | 32.86 | 0.019 | 0.470 | 0.702 | 109.4 | 0.055 | 0.015 |
| CV (%) | 41.23 | 28.59 | 25.58 | 25.96 | 26.16 | 26.96 | 19.53 |

TABLE 7

Mean Values of Pharmacokinetic Parameters Obtained for Each Rat Separately (column A) and Model-Independent Pharmacokinetic Parameters of Theophylline Calculated by Mean Values of Concentrations of Theophylline (column B); Group 1.

| PARAMETERS | A | B |
|---|---|---|
| $C_{max}$ (µg/ml) | 195.2 ± 32.9 | 176.70 |
| $K_{el}$ (h$^{-1}$) | 0.164 ± 0.02 | 0.149 |
| $T_{1/2}$ (h) | 4.504 ± 0.47 | 4.655 |
| MRT (h) | 6.6239 ± 0.70 | 6.826 |
| $Cl_t$ (ml/min) | 0.497 ± 0.055 | 0.4642 |
| $V_d$ (l) | 0.186 ± 0.015 | 0.1871 |
| $AUC_{0-\infty}$ (µg · h/ml) | 1024 ± 109 | 1034 |

Pharmacokinetics of theophylline in rats treated with CRE—Theophylline is rapidly absorbed in the blood. Maximal concentration in serum is 142.5 µg/ml 60 minutes after drug administration. Then, theophylline concentration decreased exponentially, and after 480 minutes was about 32 µg/ml (Table 8 and FIG. 4). Main pharmacokinetic parameters are shown in Tables 9 and 10.

TABLE 8

Concentration (mg/l) of Theophylline in Rat Serum (Group 2) After Oral Administration of Aminophylline

| Series, No | Time (min), after oral administration | | | | | | |
|---|---|---|---|---|---|---|---|
| | 15 | 30 | 60 | 120 | 240 | 360 | 480 |
| 1 | 161.40 | 30.54 | 120.37 | 96.55 | 134.64 | 233.16 | 56.71 |
| 2 | 98.74 | 154.41 | 158.89 | 68.74 | 148.86 | 91.61 | 33.96 |
| 3 | 8.06 | 81.52 | 119.72 | 91.30 | 115.97 | 38.01 | 12.51 |
| 4 | 192.873 | 190.52 | 108.78 | 205.63 | 89.87 | 35.31 | 7.16 |
| 5 | 144.71 | 145.07 | 158.01 | 140.04 | 65.03 | 7.61 | 34.98 |
| 6 | 164.57 | 223.28 | 189.11 | 180.859 | 61.82 | 20.21 | 45.36 |
| Mean | 128.4 | 137.60 | 142.50 | 130.50 | 102.70 | 70.99 | 31.78 |
| SD | 66.61 | 70.83 | 31.07 | 54.36 | 36.28 | 84.48 | 18.97 |
| SE | 27.19 | 28.92 | 12.69 | 22.19 | 14.81 | 34.49 | 7.743 |
| CV (%) | 51.88 | 51.49 | 21.81 | 41.65 | 35.33 | 119.0 | 59.68 |

Dose of theophylline was 192 mg/kg. Mean weight of rats was 149.9 g.

TABLE 9

Model-Independent Pharmacokinetic Parameters of Theophylline (Group 2)

| Series No | $C_{max}$ (µg/ml) | $K_{el}$ (h$^{-1}$) | $T_{1/2}$ (h) | MRT (h) | $AUC_{0-\infty}$ (µm · h/ml) | $Cl_t$ (ml/min) | $V_d$ (l) |
|---|---|---|---|---|---|---|---|
| 1 | 161.4 | 0.216 | 3.207 | 6.458 | 1443.0 | 0.3326 | 0.0923 |
| 2 | 158.9 | 0.1524 | 4.549 | 6.659 | 1141.0 | 0.421 | 0.1657 |
| 3 | 119.7 | 0.2522 | 2.749 | 4.261 | 658.9 | 0.7288 | 0.1734 |
| 4 | 192.9 | 0.3971 | 1.746 | 2.833 | 797.0 | 0.6023 | 0.091 |
| 5 | 158.0 | 0.3276 | 2.116 | 3.057 | 645.2 | 0.7439 | 0.1363 |
| 6 | 223.3 | 0.2783 | 2.491 | 3.438 | 837.3 | 0.5733 | 0.1236 |
| Mean | 169.0 | 0.2706 | 2.810 | 4.451 | 920.4 | 0.5670 | 0.1304 |
| S.D. | 35.30 | 0.0856 | 0.990 | 1.705 | 312.4 | 0.1643 | 0.035 |
| S.E. | 14.41 | 0.035 | 0.404 | 0.696 | 127.5 | 0.0671 | 0.014 |
| C.V. % | 20.88 | 31.62 | 35.24 | 38.29 | 33.94 | 28.98 | 26.96 |

TABLE 10

Mean Values of Pharmacokinetic Parameters Obtained for Each Rat Separately (column A) and Model-Independent Pharmacokinetic Parameters of Theophylline Calculated by Mean Values of Concentrations of Theophylline (column B); Group 2

| PARAMETERS | A | B |
|---|---|---|
| $C_{max}$ (µg/ml) | 169.0 ± 14.41 | 142.5 |
| $K_{el}$ (h$^{-1}$) | 0.271 ± 0.035 | 0.2042 |
| $T_{1/2}$ (h) | 2.810 ± 0.404 | 3.395 |
| MRT (h) | 4.451 ± 0.696 | 5.143 |
| $Cl_t$ (ml/min) | 0.567 ± 0.067 | 0.502 |
| $V_d$ (l) | 0.130 ± 0.014 | 0.1475 |
| $AUC_{0-\infty}$ (µg · h/ml) | 920.4 ± 128 | 956.0 |

Pharmacokinetics of theophylline in rats treated with *Hypericum* extract (Jarsin 300)—Theophylline is rapidly absorbed in blood. Maximal concentration in the serum is 41.6 µg/ml 60 minute after drug administration. Then the theophylline concentration decreased exponentially, and after 480 minutes was about 9.3 µg/ml (Table 11 and FIG. 4). The main pharmacokinetic parameters are shown in Tables 12–14.

TABLE 11

Concentration (mg/l) of Theophylline in Rat Serum (Group 3) After Oral Administration of Aminophylline

| Series, No | Time (min), after oral administration ||||||| 
|---|---|---|---|---|---|---|---|
| | 15 | 30 | 60 | 120 | 240 | 360 | 480 |
| 1 | 3.72 | 10.67 | 84.22 | 34.27 | 12.58 | 16.37 | 7.86 |
| 2 | 4.52 | 18.43 | 40.92 | 26.94 | 27.15 | 20.37 | 10.08 |
| 3 | 6.64 | 25.01 | 23.33 | 16.13 | 4.46 | 5.85 | 2.34 |
| 4 | 4.86 | 34.73 | 30.97 | 44.11 | 16.77 | 11.58 | 5.71 |
| 5 | 5.81 | 27.80 | 34.52 | 20.84 | 19.04 | 27.76 | 7.71 |
| 6 | 5.45 | 36.11 | 35.70 | 44.23 | 18.75 | 12.13 | 21.66 |
| Mean | 5.167 | 25.46 | 41.61 | 31.09 | 16.46 | 15.68 | 9.277 |
| SD | 1.027 | 9.728 | 21.67 | 11.82 | 7.554 | 7.674 | 6.622 |
| SE | 0.419 | 3.972 | 8.848 | 4.825 | 3.084 | 3.133 | 2.704 |
| CV (%) | 19.87 | 38.21 | 52.09 | 38.02 | 45.90 | 48.95 | 71.77 |

Dose of theophylline was 192 mg/kg. Mean weight of rats was 149.9 g.

TABLE 12

Model-Independent Pharmacokinetic Parameters of Theophylline (Group 3)

| Series, No | $C_{max}$ (µg/ml) | $K_{e1}$ (h$^{-1}$) | $t_{1/2}$ (h) | MRT (h) | $AUC_{0-\infty}$ (µm · h/ml) | $Cl_t$ (ml/min) | $V_d$ (l) |
|---|---|---|---|---|---|---|---|
| 1 | 84.22 | 0.2928 | 2.368 | 3.841 | 209.5 | 2.291 | 0.4696 |
| 2 | 40.92 | 0.1701 | 4.076 | 6.414 | 254.5 | 1.886 | 0.6655 |
| 3 | 25.01 | 0.3126 | 2.217 | 3.345 | 83.03 | 5.781 | 1.110 |
| 4 | 34.73 | 0.2699 | 2.569 | 3.965 | 188.9 | 2.541 | 0.565 |
| 5 | 34.52 | 0.148 | 4.679 | 7.139 | 245.9 | 1.952 | 0.7906 |
| 6 | 44.23 | 0.129 | 5.379 | 7.960 | 305.3 | 1.572 | 0.732 |
| Mean | 43.94 | 0.2204 | 3.548 | 5.444 | 214.5 | 2.671 | 0.722 |
| SD | 20.80 | 0.080 | 1.344 | 1.965 | 75.89 | 1.56 | 0.222 |
| SE | 8.492 | 0.033 | 0.5487 | 0.8022 | 30.98 | 0.637 | 0.091 |
| CV (%) | 47.34 | 36.48 | 37.88 | 36.10 | 35.38 | 58.43 | 30.77 |

TABLE 13

Mean Values of Pharmacokinetic Parameters Obtained for Each Rat Separately (column A) and Model-Independent Pharmacokinetic Parameters of Theophylline Calculated by Mean Values of Concentrations of Theophylline (column B); Group 3

| PARAMETERS | A | B |
|---|---|---|
| $C_{max}$ (µg/ml) | 43.94 ± 8.49 | 41.61 |
| $K_{e1}$ (h$^{-1}$) | 0.220 ± 0.033 | 0.2022 |
| $T_{1/2}$ (h) | 3.548 ± 0.549 | 3.428 |
| MRT (h) | 5.444 ± 0.559 | 5.358 |
| $Cl_t$ (ml/min) | 2.671 ± 0.637 | 2.310 |
| $V_d$ (l) | 0.722 ± 0.091 | 0.6853 |
| $AUC_{0-\infty}$ (µg · h/ml) | 214.5 ± 30.98 | 207.8 |

TABLE 14

Comparison of Pharmacokinetic Parameters of Theophylline in Group 1 (Control), Group 2 (Treatment with CRE), and Group 3 (Treatment with Jarsin 300)

| PARAMETERS | Group 1 | Group 2 | Group 3 |
|---|---|---|---|
| $C_{max}$ (µg/ml) | 195.2 ± 32.9 | 169.0 ± 14.41 | 43.94 ± 8.49 |
| $K_{e1}$ (h$^{-1}$) | 0.164 ± 0.02 | 0.271 ± 0.035 | 0.220 ± 0.033 |
| $t_{1/2}$ (h) | 4.504 ± 0.47 | 2.810 ± 0.404 | 3.548 ± 0.549 |
| MRT (h) | 6.6239 ± 0.70 | 4.451 ± 0.696 | 5.444 ± 0.559 |
| $Cl_t$ (ml/min) | 0.497 ± 0.055 | 0.567 ± 0.067 | 2.671 ± 0.637 |
| $V_d$ (l) | 0.186 ± 0.015 | 0.130 ± 0.014 | 0.722 ± 0.091 |
| $AUC_{0-\infty}$ (µg · h/ml) | 1024 ± 109 | 920.4 ± 128 | 214.5 ± 30.98 |

Figure 4:
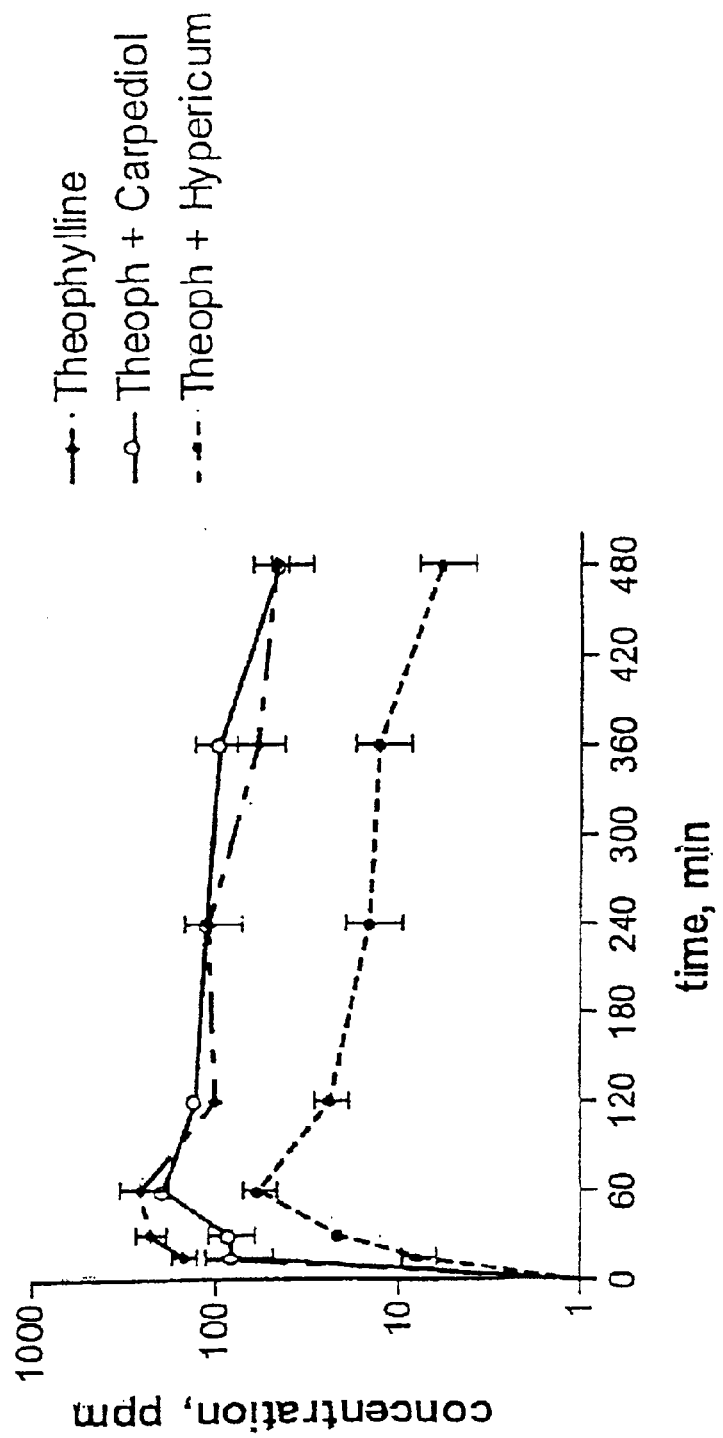
FIG. 4 shows serum concentration of theophylline versus time after oral administration of aminophylline in conjunction with Carpediol or *Hypericum* extracts, wherein the dose of aminophylline was 240 mg/kg to rats (n=6 in each point).

Discussion—FIG. 4 shows that the pharmacokinetics of theophylline is similar in all three groups and is well described by one compartment pharmacokinetic model. Combined treatment with CRE does not have any effect on the pharmacokinetics of theophylline, while *Hypericum* extract significantly decreases concentration of theophylline in blood of animals. Thus, total clearance and apparent volume of distribution of theophylline increased 5–6 times presumably due to activation of liver enzymes which reduces the therapeutic effect of theophylline. In contrast, CRE does not have such a negative effect as *Hypericum* has. These data indicate that CRE may be used as an antidepressant agent in patients which use theophylline or other drugs which can be easily metabolized by liver enzymes.

Conclusions—A new validated method of analysis of theophylline in blood was developed using capillary electrophoresis. CRE has no effect on the pharmacokinetics of theophylline in rats, while *Hypericum* extract significantly increases total clearance and decreases the concentration of theophylline in blood of rats. Thus, CRE extract has advantages over *Hypericum* as an antidepressant due to its lack of side effects on activity of other concomitantly used drugs such as theophylline.

Example 5

Clinical Report: Carpediol in Mild to Moderate Depression: A Randomized Double-Blind Placebo-Controlled Parallel Group Study The aim of this study was to investigate the therapeutic efficacy and safety of a standardized Carpediol extract compared to placebo. The relationship between two different doses (2 tablets per day and 4 tablets per day) and the antidepressant efficacy of Crassulaceae extract was examined.

Materials and Methods

Study drug: verum tablets—Carpediol standardized extract 170 mg (containing approximately 4.5 mg of compound I), calcii phosphas dibasicus, solani amylum, cellulosum microcristallinum, magnesii stearas, and silica colloidalis anh.

Placebo Tablet—Lactose 170 mg, calcii phosphas dibasicus, solani amylum, cellulosum microcristallinum, magnesii stearas, and silica colloidalis anh.

Coating for both verum/placebo—Saccharose, calcium carbohydrate, magnesium silicate, polyvinylpyrrolidone, and titanium dioxide.

The test medication (verum and placebo) was manufactured according to Good Manufacturing Practice (GMP) by Swedish Herbal Institute (SHI) in the form of white, sugar-coated tablets. Verum and placebo tablets were produced with identical organoleptic appearance and they were indistinguishable from each other. Each package of tablets contained 60 tablets to be taken once daily for 14 days. The medication was divided into two sets of plastic jars which were labelled: Carpediol Clinical A, and Carpediol Clinical B. An identification number was noted in a protocol to allow for subsequent identification after the completion of the study to perform statistical analysis. The information on the placebo and the active substance became available to the investigators and volunteers only after the completion of study and after the statistical analysis was performed. The study was performed in compliance with the revised declaration of Helsinki (Hong Kong 1989).

Study design—The investigation was conducted as a double-blind, randomized, parallel, group evaluation of two different daily dosages of Carpediol standardized extract versus placebo. Patients were selected from in- and outpatients of State Medical University Neurology Department at "Erebouni" Medical Center. All eligible patients underwent a two week running-in period without any medication both for individuals receiving or who have received recently any antidepressant or psychotropic medication. All patients after the running-in period were randomized using principles of total randomization, to one of three following treatment groups:

(1) Group I received 2 tablets of Carpediol standardized extract (340 mg/day at bedtime once daily);
(2) Group II received 4 tablets of Carpediol standardized extract (680 mg/day at bedtime once daily); and
(3) Group III received 2 tablets of placebo (340 mg/day at bedtime once daily).

The study drugs were dispensed as film-coated tablets, which were identical in all aspects of their appearance.

After being randomized the patients underwent six-week period of double-blind treatment. All patients during the treatment period were followed-up by telephone contacts or personally by attending physicians, and for safety assessment, adverse events were documented during all contacts. Compliance was documented by tablet count on the last visit. All data included signed written consent, personal information, clinical report, medical history, results of HAMD and BDI assessments and possible adverse reactions and reasons for study termination were collected in a Patient Journal, signed by principal investigator and the monitor.

The primary efficacy variable was the change in the HAMD total scores between day 0 and treatment end (day 42–44). The secondary efficacy variables were the changes in the four HAMD symptom indicator subgroups (insomnia, somatization, emotional instability, and low self-esteem) reflecting the different somatic and physiological aspects of mild and moderate depression between day 0 and treatment end (day 42–44). HAMD subgroup I included items 4, 5 and 6 in the HAMD questionnaire (insomnia), HAMD subgroup II included items 9 and 10 (emotional instability), HAMD subgroup III included items 12–16 (somatization and hypochondrials), and HAMD subgroup IV included items 17 and 18 (self-rating).

Patient inclusion criteria—The participants included in the study were male and female patients with mild or moderate depression according to DSM-IV inclusion criteria. Eligible patients were between 18 and 70 years old and were required to have an initial score $\geq 13$ on the Beck Depression Inventory (BDI, short form, 13-item Armenian and Russian localized version), and $\geq 21$ on the Hamilton Rating Scale for Depression (HAMD, 21-item Armenian and Russian localized version). All tests were performed by skilled physicians using Armenian and Russian versions simultaneously to avoid possible misinterpretations.

Patient exclusion criteria—Major exclusion criteria were: previously documented or reported attempt to commit suicide or $\geq 2$ on HAMD item 3 or $\geq 1$ on BDI item H (suicidality), progressive organic or metabolic brain syndrome, compulsive, schizophrenic or other delusive disorders, pregnancy or lactation. A 2 week wash-out period was required for those who were previously treated by any medication with possible psychotropic effects. Patients suffering from serious chronic illness such as cardiovascular diseases, diabetes and so on receiving appropriate medication with possible drug interactions were also excluded.

Sample size—Assuming a 30% effect difference between 2 treatment groups and the placebo group between points in time with a 95% confidence interval and a maximal drop-out of 20%, a sample size of (2×30) was calculated as sufficient for a (1–5%) significance level. The analyses were performed after 91 patients had been included in the baseline, out of which 89 patients had been randomized into 3 groups (30 patients in placebo group, 31 patients in 2 tablets/day group and 30 patients in 4 tablets/day group). Two (2) patients canceled their participation in the study due to non medical causes. The rest of the 89 patients were evaluated according to the intention-to-treat principle.

Efficacy parameters—Efficacy in depressive complaints was assessed on days 0 and days 42 after implementation of the 6-week treatment period, using the Hamilton Rating Scale for Depression (HAMD, 21-item Armenian and Russian localized synchronized version). The primary efficacy variable was the change in the HAMD total scores between day 0 and treatment end (day 42–44). The secondary efficacy variables were the changes in the four HAMD subgroups reflection the proportion of different somatic and physiological aspects of mild and moderate depression between day 0 and treatment end (day 42–44).

Safety parameters—All patients included in the study underwent routine blood check-up before and after the implementation of the treatment, as well as general medical investigation. All complaints due to the study medication were documented by the attending principal investigator, physicians and monitors. No toxic side effect was reported during the study.

Statistical methods—Each patient was identified by a number and trial identification number. The data were entered into the database patient by patient. The study was planned with an adaptive interim analyses after treatment of 3×30 patients (57). The overall type 1 error rate was settled as $\alpha=0.05$, which implied a nominal level of $\alpha=0.0299$ for the assessment of the statistical significance in the interim analyses. A sample size of 30 patients per group enables detection of a standardized treatment difference of 0.50 with a power of 80% (two-sample t-test, $\alpha=0.05$, one-sided). Statistical analysis of mean values was performed according to Student's test and Wilcoxon non-parametric two tailed rank test. Pearson's correlation was used to test for correlation between variables. Data management and calculations were performed with PRISM Statistical Software Version 2.01, 1996. The results are collated in Tables 15–22.

TABLE 15

Anthropocentric data

|  | Male | Female | Mean value age | SD |
|---|---|---|---|---|
| Verum 2 tablets/day group (n = 31) | 10 (32.3%) | 21 (67.7%) | 44.90 | 11.54 |
| Verum 4 tablets/day group (n = 29) | 12 (41.4%) | 17 (58.6%) | 44.66 | 25.49 |
| Placebo (n = 29) | 14 (48.3%) | 15 (51.7%) | 42.80 | 12.87 |

TABLE 16

Mean values of age, height and weight of patients involved in the study

|  | Placebo group (n = 29) | 2 tablets/day group (n = 31) | 4 tablets/day group (n = 29) |
|---|---|---|---|
| Age (years) | 53.3 ± 10.2 | 44.9 ± 11.5 | 51.4 ± 9.5 |
| Height (cm) | 165.8 ± 8.3 | 165.7 ± 8.8 | 166.8 ± 9.6 |
| Weight (kg) | 73.7 ± 14.9 | 68.1 ± 13.1 | 71.5 ± 10.8 |

TABLE 17

Intergroup Statistics

|  | Number of participants | Mean value age | SD |
|---|---|---|---|
| Placebo | 29 | 42.80 | 11.54 |
| Verum | 60 | 44.78 | 18.52 |

Figure 5:
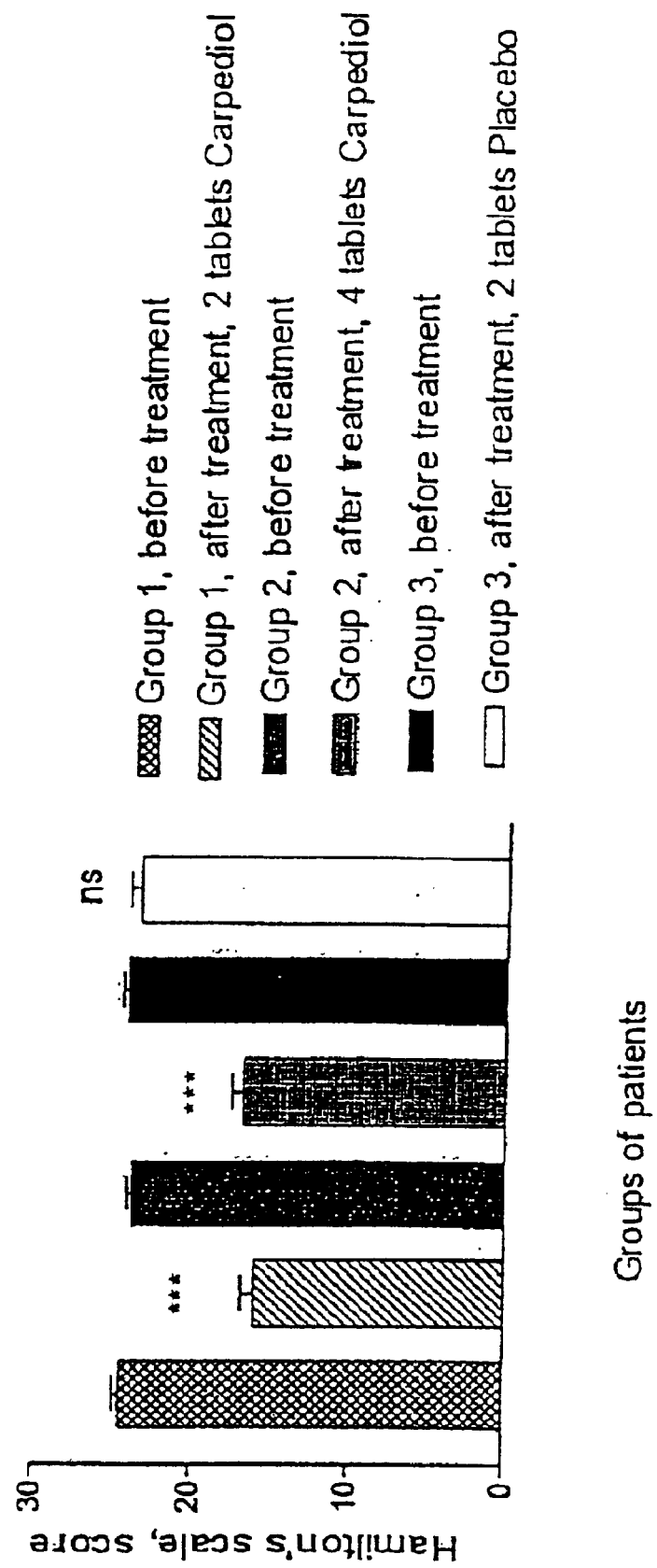
FIG. 5 shows results of treatment in different groups: Hamilton scale total scores before and after the treatment.
Figure 6:
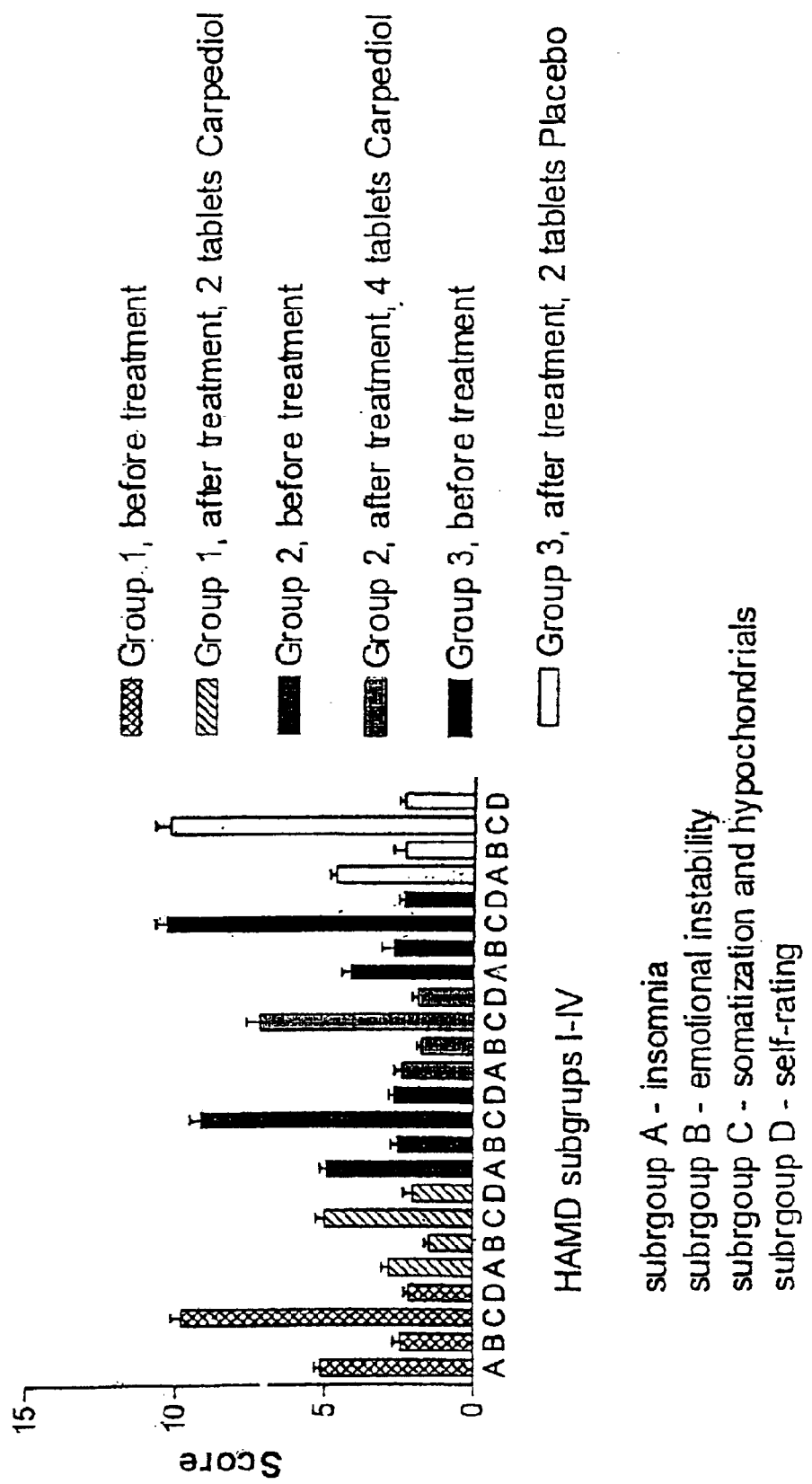
FIG. 6 shows differences in HAMD subgroups between different treatment groups before treatment.

The study was planned with adaptive interim analyses after treatment of 90 (3 groups of 30) patients. Eighty-nine (89) patients with mild to moderate depression completed the study within their treatment group without any reported adverse effect and were included in the statistical analysis. The results are summarized in Tables 18–22 and FIGS. 5 and 6.

TABLE 18

Hamilton Scale Total Scores

| Groups | I - Carpediol 2 tablets | | II - Carpediol 4 tablets | | III - Placebo 2 tablets | |
|---|---|---|---|---|---|---|
| Day of treatment | 0 | 42 | 0 | 42 | 0 | 42 |
| Number of patients | 31 | 31 | 29 | 29 | 29 | 29 |
| Mean HAMD score | 24.52 | 15.97 | 23.79 | 16.72 | 24.17 | 23.41 |
| Std. Deviation | 2.249 | 4.637 | 1.698 | 4.174 | 1.692 | 3.803 |
| Std. Error | 0.4039 | 0.8328 | 0.3154 | 0.7751 | 0.3142 | 0.7063 |
| Lower 95% CI | 23.69 | 14.27 | 23.15 | 15.14 | 23.53 | 21.97 |
| Upper 95% CI | 25.34 | 17.67 | 24.44 | 18.31 | 24.82 | 24.86 |
| Coefficient of variation | 9.17% | 29.04% | 7.14% | 24.96% | 7.00% | 16.24% |
| Geometric mean | 24.42 | 15.23 | 23.74 | 16.25 | 24.12 | 23.04 |

DIFFERENCE BEFORE AND AFTER TREATMENT

| Groups | I - Carpediol 2 tablets | II - Carpediol 4 tablets | III - Placebo 2 tablets |
|---|---|---|---|
| Paired t test, days | 0–42 | 0–42 | 0–42 |
| P value | P < 0.0001 | P < 0.0001 | ns |
| P value summary | *** | *** |  |
| Therapeutic effect | Yes | Yes | No |

DIFFERENCE BETWEEN GROUPS BEFORE TREATMENT

| Paired t test, groups | I to III | I to II | II to III |
|---|---|---|---|
| P value summary | ns | ns | ns |

No difference between groups before treatment

DIFFERENCE BETWEEN GROUPS AFTER TREATMENT

| Paired t test, groups | I to III | II to III |
|---|---|---|
| P value | P < 0.0001 | P < 0.0001 |
| P value summary | *** | *** |

A difference is seen between the groups treated with Carpediol (I and II) and group III (placebo)

TABLE 19

Difference in HAMD Subgroups Between Different Treatment Groups Before Treatment

| Parameter | Insomnia | | |
|---|---|---|---|
| Paired t test, groups | I to III | II to III | I to II |
| P value | 0.0139 | 0.0413 | 0.5930 |
| P value summary | * | * | ns |

There is a difference between groups I and III, and II and III;
No difference between I and II before treatment

| Parameter | Emotional | | |
|---|---|---|---|
| Paired t test, groups | I to III | II to III | I to II |
| P value | 0.6144 | 0.7686 | 0.7500 |
| P value summary | ns | ns | Ns |

TABLE 19-continued

Difference in HAMD Subgroups Between Different Treatment Groups Before Treatment No difference in any groups

| Parameter | Somatic | | |
|---|---|---|---|
| Paired t test, groups | I to III | II to III | I to II |
| P value | 0.2948 | 0.0285 | 0.2142 |
| P value summary | ns | * | Ns |

There is a difference between groups II and III, no difference between groups I and III, I and II

| Parameter | Self estimation | | |
|---|---|---|---|
| Paired t test, groups | I to III | II to III | I to II |
| P value | 0.4403 | 0.2297 | 0.0412 |
| P value summary | Ns | Ns | * |

A difference is seen between groups I and II, but no difference is seen between groups I and III, and II and III

TABLE 20

Group I - Carpediol 2 Tablets

| Parameter | Insomnia | Emotional | Somatic | Self estimation | Ins | Emot | Som | Self |
|---|---|---|---|---|---|---|---|---|
| Day of treatment | 0 | 0 | 0 | 0 | 42 | 42 | 42 | 42 |
| Number of patient | 31 | 31 | 31 | 31 | 31 | 31 | 31 | 31 |
| Mean, score | 5.129 | 2.484 | 9.806 | 2.194 | 2.871 | 1.452 | 5.000 | 2.032 |
| Std. Deviation | 1.204 | 1.338 | 1.990 | 0.8725 | 1.384 | 1.121 | 1.789 | 1.975 |
| Std. Error | 0.2162 | 0.2404 | 0.3575 | 0.1567 | 0.2486 | 0.2013 | 0.3213 | 0.3546 |
| Lower 95% CI | 4.687 | 1.993 | 9.076 | 1.874 | 2.363 | 1.041 | 4.344 | 1.308 |
| Upper 95% CI | 5.571 | 2.975 | 10.54 | 2.514 | 3.379 | 1.863 | 5.656 | 2.757 |
| Coefficient of variation | 23.47% | 53.88% | 20.30% | 39.78% | 48.22% | 77.20% | 35.78% | 97.16% |

Difference before and after treatment

| | Insomnia | Emotions | Somatic | Self estimation |
|---|---|---|---|---|
| Paired t test, days | 0–42 | 0–42 | 0–42 | 0–42 |
| P value | P < 0.0001 | P < 0.0001 | P < 0.0001 | 0.6428 |
| P value summary | *** | *** | *** | ns |

After treatment, positive effect is seen in insomnia, emotions, somatic; no effect in self estimation

TABLE 21

Group II - Carpediol 4 Tablets

| Parameter | Insom | Emot | Somat | Self estimation | Insom | Emot | Som | Self est |
|---|---|---|---|---|---|---|---|---|
| Day of treatment | 0 | 0 | 0 | 0 | 42 | 42 | 42 | 42 |
| Number of patients | 29 | 29 | 29 | 29 | 29 | 29 | 29 | 29 |
| Mean | 4.966 | 2.586 | 9.138 | 2.690 | 2.414 | 1.759 | 7.207 | 1.897 |
| Std. Deviation | 1.149 | 1.119 | 2.133 | 0.9675 | 1.476 | 1.023 | 2.498 | 0.9002 |
| Std. Error | 0.2134 | 0.2077 | 0.3962 | 0.1797 | 0.2742 | 0.1900 | 0.4639 | 0.1672 |
| Lower 95% CI | 4.528 | 2.161 | 8.326 | 2.322 | 1.852 | 1.369 | 6.257 | 1.554 |
| Upper 95% CI | 5.403 | 3.012 | 9.949 | 3.058 | 2.975 | 2.148 | 8.157 | 2.239 |
| Coefficient of variation | 23.14% | 43.25% | 23.35% | 35.97% | 61.17% | 58.18% | 34.67% | 47.46% |

Difference before and after treatment

| | Insomnia | Emotions | Somatic | Self est |
|---|---|---|---|---|
| Paired t test, days | 0–42 | 0–42 | 0–42 | 0–42 |
| P value | P < 0.0001 | 0.0009 | 0.0005 | 0.0002 |
| P value summary | *** | *** | *** | *** |

After treatment, positive effect is seen in all parameters

TABLE 22

| | Group III - Placebo Tablets | | | | | | | |
|---|---|---|---|---|---|---|---|---|
| Parameter | Insom | Emot | Somat | Self est | Ins | Emot | Som | Self |
| Day of treatment | 0 | 0 | 0 | 0 | 42 | 42 | 42 | 42 |
| Number of values | 29 | 29 | 29 | 29 | 29 | 29 | 29 | 29 |
| Mean | 4.172 | 2.724 | 10.34 | 2.379 | 4.655 | 2.345 | 10.24 | 2.379 |
| Std. Deviation | 1.692 | 2.250 | 1.951 | 0.9788 | 1.233 | 2.208 | 2.734 | 0.9416 |
| Std. Error | 0.3142 | 0.4179 | 0.3622 | 0.1818 | 0.2289 | 0.4101 | 0.5077 | 0.1749 |
| Lower 95% CI | 3.529 | 1.868 | 9.603 | 2.007 | 4.186 | 1.505 | 9.201 | 2.021 |
| Upper 95% CI | 4.816 | 3.580 | 11.09 | 2.752 | 5.124 | 3.185 | 11.28 | 2.737 |
| Coefficient of variation | 47.46 | 40.55% | 82.61% | 18.86% | 41.14% | 26.48% | 94.18% | 26.70% |

| | Difference before and after treatment | | | |
|---|---|---|---|---|
| | Insomnia | Emotions | Somatic | Self est. |
| Paired t test, days | 0–42 | 0–42 | 0–42 | 0–42 |
| P value | 0.1609 | 0.2393 | 0.8382 | 1.0000 |
| P value summary | ns | ns | ns | ns |

No effect is seen after treatment

Discussion—Total HAMD scores in all treatment groups are presented in Table 18. There were no statistically significant differences in mean values between the groups before the beginning of the treatment (24.52 in the two-tablet group; 23.79 in the four-tablet group; and 24.17 in the placebo group, p=ns). Both groups administered with Carpediol standardized extract tablets exhibited significantly reduced total level of depression after 42 days of treatment. Thus, in the two-tablet group, the total HAMD score declined from 24.52 to 15.97, p<0.0001; and in the four-tablet group, the total HAMD score declined from 23.79 to 16.72, p<0.0001. There was no improvement in the group receiving placebo (mean HAMD score was 24.17 before the treatment and remained 23.41 after the treatment, p=ns).

Statistical comparisons within different modalities of mild and moderate depression were presented as HAMD subgroups or subscores as shown in Table 19. Most modalities have the same intensity in the three evaluated groups before the beginning of the treatment. However, a divergence in the strength of insomnia was found between the experimental and placebo groups. As shown in Tables 19–22, the basic level of insomnia was even higher in groups receiving Carpediol standardized extract. The mean value of insomnia in the two-tablet group was 5.129 versus 4.17 in the placebo group, p=0.0139, and 4.966 in the four-tablet group versus 4.17 in the placebo group, p=0.0413.

The effectiveness of Carpediol standardized extract is shown in Tables 19 and 20. In the two-tablet group, statistically significant improvement in insomnia, emotional instability and the level of somatization is seen. The low self estimation level remained unchanged after treatment with two tablets of Carpediol standardized extract. However, the 42 daily treatment with four tablets of Carpediol standardized extract showed significant improvement in this modality of depression as well (2.690 before treatment and 1.897 after the treatment, p=0.0002). All other modalities of mild and moderate depression also significantly improved after the treatment with four tablets of Carpediol standardized extract. In the group receiving placebo, we did not find any improvement in any modality of depression.

We conclude that Carpediol standardized extract tablets have high antidepressive potency in patients with mild to moderate depression. Carpediol standardized extract in dosages of either two or four tablets taken daily in a six week period significantly reduced the total level of depression, and affects such aspects of depression as insomnia, emotional instability and somatization. The low self estimation remained unchanged when administered daily with two tablets of Carpediol standardized extract, however, this indicator improved significantly at a higher dose of Carpediol standardized extract.

Summary—Thus, in a randomized double-blind placebo-controlled study the clinical efficacy and safety of standardized extract of the rhizome Carpediol were investigated in 89 male and female outpatients suffering from mild to moderate depression according to DSM-IV diagnostic, criteria verified by Beck Depression Inventory (BDI, short form, 13-item) and Hamilton Rating Scale for Depression (HAMD, 21-item), Armenian and Russian localized versions. After a 2 week drug-free run-in period patients were randomized into one of three treatment groups: I) 2 tablets of Carpediol standardized extract (340 mg/day at bedtime once daily); II) 4 tablets of Carpediol standardized extract (680 mg/day at bedtime once daily); III) 2 tablets of placebo (340 mg/day at bedtime once daily). The efficacy in depressive complaints was assessed on day 0 and day 42 after implementation of the 6-week treatment period, using the HAMD total scores and the four specific subgroups reflecting levels of insomnia, emotional instability, somatization and self estimation. At the end of the treatment period (day 42), the patients receiving Carpediol standardized extract exhibited the largest HAMD reduction versus at day 0. Patients receiving a lower dose of Carpediol standardized extract (2 tablets daily) followed in their efficacy. The placebo group did not reveal any improvement. All aspects of mild to moderate depression improved, including insomnia, somatization, emotional instability and low self estimation (or low self esteem).

All of the references cited herein are incorporated by reference in their entirety.

REFERENCES

1. Judd, L., Int. *Clin. Psychopharmacol.* 10 (Suppl.4) 5–10, 1995.
2. Von Korff M, Shapiro S, Burke J D, et al. *Arch Gen Psychiatry;* 44:152–156, 1987.
3. Wells K B, Golding J M, Burnham M A. *Am J Psychiatric;*145:976–981, 1988.
4. Communication from the Medical Product Agency, Sweden, Dec. 1, 1999; *FDA Public Health Advisory. Risk of Drug Interactions with St. John's Wort and Indinavir* and *Other Drugs*, Feb. 10, 2000; http://www.fda.gov/cder/drug/advisory/stjwort.htm; http://www.open.gov.uk/mca/mchome.htm).
5. Steinegger-Hänsel: Farmakognosie, 5:e *Auflage*, 613, 1992
6. Saratikov, A. S. et al., in: *Die Pharmazie* 23: 392–395, 1968.
7. Hjaltalin, J.: *Botany of Iceland*, Oslo, 237, 1830.
8. Hoeg, O. A.: *Våre Medicinske Planter*, Det Beste, Oslo, 237, 1984.
9. Roselli, C.: En liten dock mycket nyttig örtabok eller Den lille Naturläkaren, book, C. Topelius, 1755 (Facsimile C. Topelius, 1974).
10. Sandberg, F., Hansen, H. A.: "Örtmedicin och växtmagi, Publishing house: Reader's Digests AB, Stockholm, 233, 1998.
11. Sandberg, F., Bohlin, L.: Fytoterapi—växtbaserade l äkemedel, Hälsokostrådets förlag, 131, 1993.
12. *Pharmacopée Française*, IX edition, 214/100, 1974.
13. *Materia Medica*, Linné, C, *Liber I. de Plantis*, 168, 1749.
14. Virey, J.-J.: Traité de pharmacie théorique et pratique. Paris, 92, 1811.
15. Saratikov, A. S., *The CNS stimulants*, Tomsk University Press, 3–23, 1966.
16. Tsarong, T. J.: *Handbook of Traditional Tibetan Drugs*, Tibetan Medical Publications, Kalimpong, India, 1986.
17. Li Y., Tibetan Medical Dictionary, *Chinese Journal of Ethnomedicine and Ethnopharmacy*, 14: 16–19, 1995.
18. Muravijeva, D. A.: Pharmacognosy (With fundamentals of biochemistry of medicinal herbs), Publisher Meditsina, 1978.
19. Mashkovskij, M. D.: Medicines (Manual on Pharmacotherapy for doctors) Part I, Eight revised and amended, Publ. Meditsina, Moscow, 1977.
20. Turova, A. D., Sapozhnikova, E. N.: Medicinal Plants of the USSR and Their Use, Fourth edition, Moscow, Publisher Meditsina, 1984.
21. Müller-Dietz, H.: Arzneipflanzen der Sowietunion, Book, Freien Universität, 91–92, 1970.
22. Wagner, H., Norr, H., Winterhoff, H.: *Phytomedicine* 1: 63–76, 1994.
23. Brekhman, I. I., Dardymov, I. V.: *Ann. Rev. Pharmacol.* 9: 419–430, 1969.
24. Azizov, A. P., Seifulla, R. D.: *Eksp. Klin.Farmakol* 61(3): 61–63, 1998.
25. Porsolt R D, Anton G, Blavet N, Jalfre M.: *Eur J Pharmacol* 47:379–391, 1978.
26. Porsolt R D, Bertin A, Jalfre M.: Arch Int Pharmacodyn 229:327–336, 1977.
27. Porsolt R D, Le Pichon M, Jalfre M Nature 266:730–732, 1977.
28. Chatterjee S S, Noldner M., Koch E., Erdelmeier C.: Pharmacopsychiatry. 31 (Suppl 1): 7–15, 1998.
29. Bhattacharya S K, Chakrabarti A., Chatterjee S S Pharmacopsychiatry. 31 (Suppl 1): 22–29, 1998.
30. Butterweck V, Jurgenliemk G, Nahrstedt A, Winterhoff H.: Planta Medica 66: 3–6, 2000.
31. Basely R. C.: Disposition of toxic drugs and chemicals in man, Biomed Public. Canton, C N, 1978, 2, pp.78–81.
32. Biber A., Fischer H., Romer A., Chatterjee S. S.: Pharmacopsychiatria; 1998, 31, Suppl. pp. 36–43.
33. Ramzan I. M., Levy G.: J. of Pharmacol. and Exper. Therap. 1986, 236, No 3, pp 708–713.
34. Frug-Berman A.: Lancet 2000, January8; (1998): p. 134–138.

Those skilled in the art will recognize, or be able to ascertain using no more than routine experimentation, many equivalents to the specific embodiments of the invention specifically described herein. Such equivalents are intended to be encompassed in the scope of the following claims.

What is claimed is:

1. A method for treating a symptom of depression comprising administering to a person in need thereof a composition comprising an extract of a plant belonging to Crassulaceae, wherein said extract comprises 2-(4-Hydroxyphenyl)ethyl-β-D-glucopyranoside or 3-[6-O-(α-L-arabinopyranosol)-β-D-glucopyranosol]-oxy-1-phenylpropene.

2. A method for preparing a composition comprising an extract of Crassulaceae for treating a symptom of depression, which comprises:
   a) dispersing plant matter of said Crassulaceae in an alcohol;
   b) heating said dispersed plant matter,
   c) separating the alcohol solution from said plant matter,
   d) evaporating the alcohol solution to obtain spissum,
   e) dissolving the spissum in a liquid solution,
   f) extracting the liquid solution of step e) with a salt of an acid,
   g) extracting the liquid solution of step f) with an alcohol solution, and
   i) evaporating the alcohol solution of step g) to obtain said extract.

3. The method according to claim 1, wherein said 2-(4-Hydroxyphenyl)ethyl-β-D-glucopyranoside or 3-[6-O-(α-L-arabinopyranosyl)-β-D-glucopyranosyl]-oxy-1-phenylpropene is present in the range of about 2 to about 15 dry weight percent.

4. The method according to claim 3, wherein said 2-(4-Hydroxyphenyl)ethyl-β-D-glucopyranoside or 3-[6-O-(α-L-arabinopyranosyl)-β-D-glucopyranosyl]-oxy-1-phenylpropene is present in the range of about 5 to about 15 dry weight percent.

5. The method according to claim 4, wherein said 2-(4-Hydroxyphenyl)ethyl-β-D-glucopyranoside or 3-[6-O-(α-L-arabinopyranosyl)-β-D-glucopyranosyl]-oxy-1-phenylpropene is present in the range of about 7 to about 15 dry weight percent.

6. The method according to claim 1, comprising administering additional medicine, wherein said extract substantially has no effect on the pharmacokinetics of said additional medicine.

7. The method according to claim 6, wherein said additional medicine is aminophylline or theophylline.

8. The method according to claim 1, wherein said symptom is insomnia, low self-esteem, emotional instability, or somatization.

9. The method according to claim 8, wherein said symptom is insomnia, emotional instability or somatization.

10. The method according to claim 1, wherein said depression is mild to moderate.

11. The method according to claim 1, wherein said plant belongs to the genus *Sedum* and *Sempervivum*.

12. The method according to claim 11, wherein said plant is *Sedum rosea, Sedum maximum, Sedum auglicum, Sedum aruum, Sedum quadrifida, Sedum integrefolia, Sedum telephium, Sedum algida, Sedum crenulata, Sedum pinnatifida, Sedum hybridum, Sedum aizoon, Sedum purpureum, Sedum heterodonta, Sedum viridula, Sedum kirilowii, Sedum linearifolia, Sedum gelida,* or *Sempervivum soboleferum*.

13. The method according to claim 1, wherein said extract is in tablet form.

14. A pharmaceutically acceptable composition comprising a standardized extract of a plant belonging to Crassulaceae comprising 2-(4-Hydroxyphenyl)ethyl-β-D-glucopyranoside or 3-[6-O-(α-L-arabinopyranosyl)-β-D-glucopyranosyl]oxy-1-phenylpropene.

15. The pharmaceutically acceptable composition according to claim 14, wherein said plant belongs to the genus *Sedum* and *Sempervivum*.

16. The pharmaceutically acceptable composition according to claim 15, wherein said plant is *Sedum rosea, Sedum maximum, Sedum auglicum, Sedum aruum, Sedum quadrifida, Sedum integrefolia, Sedum telephium, Sedum algida, Sedum crenulata, Sedum pinnatifida, Sedum hybridum, Sedum aizoon, Sedum purpureum, Sedum heterodonta, Sedum viridula, Sedum kirilowii, Sedum linearifolia, Sedum gelida,* or *Sempervivum soboleferum.*

17. A pharmaceutically acceptable tablet comprising a composition which comprises an extract of a plant belonging to Crassulaceae comprising 2-(4-Hydroxyphenyl)ethyl-β-D-glucopyranoside or 3-[6-O-(α-L-arabinopyranosyl)-β-D-glucopyranosyl]-oxy-1-phenylpropene.

18. A method for treating a symptom of depression comprising administering to a person in need thereof, a composition comprising 2-(4-Hydroxyphenyl)ethyl-β-D-glucopyranoside or 3-[6-O-(α-L-arabinopyranosyl)-β-D-glucopyranosyl]-oxy-1-phenylpropene, and a pharmaceutically acceptable carrier thereof.

19. The method according to claim 18, wherein said depression is mild to moderate.

* * * * *